(12) United States Patent
Lopez et al.

(10) Patent No.: US 10,639,197 B2
(45) Date of Patent: May 5, 2020

(54) VITRECTOMY PROBE

(71) Applicant: Novartis AG, Basel (CH)

(72) Inventors: Jose Luis Lopez, Cypress, CA (US); Matthew Douglas McCawley, San Clemente, CA (US); Brian William McDonell, Irvine, CA (US); Timothy C. Ryan, Laguna Hills, CA (US); John R. Underwood, Laguna Nigel, CA (US); Salomon Valencia, Aliso Viejo, CA (US); Jack Robert Auld, Laguna Niguel, CA (US)

(73) Assignee: Alcon Inc., Fribourg (CH)

( * ) Notice: Subject to any disclaimer, the term of this patent is extended or adjusted under 35 U.S.C. 154(b) by 261 days.

(21) Appl. No.: 15/793,353

(22) Filed: Oct. 25, 2017

(65) Prior Publication Data

US 2018/0360660 A1    Dec. 20, 2018

Related U.S. Application Data

(60) Provisional application No. 62/521,754, filed on Jun. 19, 2017.

(51) Int. Cl.
*A61F 9/007* (2006.01)
*A61B 17/00* (2006.01)

(52) U.S. Cl.
CPC ............ *A61F 9/00763* (2013.01); *A61B 2017/00544* (2013.01); *A61B 2017/00561* (2013.01); *A61B 2218/007* (2013.01)

(58) Field of Classification Search
CPC ............ A61F 9/00763; A61F 9/00736; A61B 17/320783; A61B 2017/320791; A61B 17/32075; A61B 17/3207; A61B 17/320758; A61B 17/320016; A61B 17/32002; A61B 2017/320028; A61B 2017/320032
See application file for complete search history.

(56) References Cited

U.S. PATENT DOCUMENTS

| | | | |
|---|---|---|---|
| 4,011,869 A | 3/1977 | Seiler, Jr. | |
| 4,314,560 A * | 2/1982 | Helfgott | A61F 9/00763 604/118 |

(Continued)

FOREIGN PATENT DOCUMENTS

| | | |
|---|---|---|
| EP | 2913034 A1 | 9/2015 |
| EP | 2863853 B1 | 11/2017 |

(Continued)

*Primary Examiner* — Gregory A Anderson

(57) ABSTRACT

In some embodiments, a vitrectomy probe may include an inner cutting tube reciprocating in an outer tube. The outer tube includes a side port and the inner tube includes a distal cutting port, and, in some embodiments, an additional side port. In some embodiments, the inner tube may also include a flat upper edge that cuts across the outer tube side port. In some embodiments, a diaphragm drives the inner tube and may have an open-stroke side with a lower hardness material than a closed-stroke side. In some embodiments, an aspiration tube coupled to the vitrectomy probe may include a first aspiration tubing and a second aspiration tubing with a lower hardness than the first aspiration tubing. In some embodiments, the vitrectomy probe may be coupled to pneumatic tubing that is stepped or tapered.

14 Claims, 15 Drawing Sheets

(56) References Cited

U.S. PATENT DOCUMENTS

| | | | |
|---|---|---|---|
| 4,530,356 A | 7/1985 | Helfgott et al. |
| 4,577,629 A | 3/1986 | Martinez |
| 4,696,298 A | 9/1987 | Higgins |
| 4,909,249 A | 3/1990 | Akkas et al. |
| 5,019,035 A | 5/1991 | Missirlian |
| 5,047,008 A | 9/1991 | de Juan, Jr. et al. |
| 5,106,364 A | 4/1992 | Hayafuji |
| 5,176,628 A | 1/1993 | Charles |
| 5,226,910 A | 7/1993 | Kajiyama |
| 5,284,472 A | 2/1994 | Sussman |
| 5,285,795 A | 2/1994 | Ryan |
| 5,458,112 A | 10/1995 | Weaver |
| 5,630,827 A | 3/1997 | Vijfvinkel |
| 5,722,945 A | 3/1998 | Anis et al. |
| 5,733,297 A | 3/1998 | Wang |
| 5,980,546 A | 11/1999 | Hood |
| 6,024,751 A | 2/2000 | Lovato |
| 6,156,049 A | 12/2000 | Lovato |
| 6,258,111 B1 | 7/2001 | Ross et al. |
| 6,383,203 B1 | 5/2002 | Makihara |
| 6,485,499 B1 | 11/2002 | Oberkamp |
| 6,575,990 B1 | 6/2003 | Wang |
| 6,773,445 B2 | 8/2004 | Finlay et al. |
| 6,875,221 B2 | 4/2005 | Cull |
| 6,890,309 B2 | 5/2005 | Fisher |
| 7,335,217 B2 | 2/2008 | Wang et al. |
| 7,600,405 B2 | 10/2009 | Maurer, Jr. |
| 8,038,692 B2 | 10/2011 | Valencia |
| 8,187,293 B2 | 5/2012 | Kirchhevel |
| 8,313,501 B2 | 11/2012 | Miller |
| 8,328,835 B2 | 12/2012 | Perkins |
| 8,608,753 B2 | 12/2013 | Luloh |
| 8,641,701 B2 | 2/2014 | Hangai |
| 8,808,318 B2 | 8/2014 | Auld |
| 9,060,841 B2 | 6/2015 | Mccawley |
| 9,101,442 B2 | 8/2015 | Mcdonell |
| 9,211,608 B2 | 12/2015 | Chen |
| 9,486,360 B2 | 11/2016 | Chon |
| 9,498,378 B2 | 11/2016 | Mcdonell |
| 9,615,969 B2 | 4/2017 | Nissan |
| 9,693,898 B2 | 7/2017 | Farley |
| 9,956,115 B2 | 5/2018 | Rieger |
| 10,070,990 B2 | 9/2018 | Mcdonell |
| 10,111,777 B2 | 10/2018 | Gunn |
| 10,369,046 B2 | 8/2019 | Mcdonell |
| 10,376,414 B2 | 8/2019 | Hallen |
| 2005/0090765 A1 | 4/2005 | Fisher |
| 2007/0185512 A1 | 8/2007 | Kirchhevel |
| 2007/0185514 A1 | 8/2007 | Kirchhevel |
| 2010/0056991 A1* | 3/2010 | Dimalanta, Jr. .... A61F 9/00736 604/35 |
| 2010/0106054 A1 | 4/2010 | Hangai |
| 2010/0312169 A1 | 12/2010 | Auld |
| 2013/0079806 A1 | 3/2013 | Peyman |
| 2013/0150875 A1* | 6/2013 | McDonell ........... A61F 9/00763 606/170 |
| 2013/0211439 A1 | 8/2013 | Geuder |
| 2015/0157503 A1 | 6/2015 | Chon |
| 2015/0182379 A1 | 7/2015 | Fantoni |
| 2015/0335485 A1 | 11/2015 | Rieger |
| 2016/0022489 A1 | 1/2016 | Hartstra |
| 2016/0135991 A1 | 5/2016 | Farley |
| 2018/0104101 A1 | 4/2018 | Lopez |
| 2018/0133057 A1 | 5/2018 | Diao |
| 2019/0038460 A1* | 2/2019 | Peterson ............. A61F 9/00825 |

FOREIGN PATENT DOCUMENTS

| | | |
|---|---|---|
| EP | 2967991 B1 | 5/2019 |
| WO | WO9846147 A1 | 10/1998 |
| WO | WO2012059092 A1 | 5/2012 |
| WO | WO2012083402 A1 | 6/2012 |
| WO | WO2014117774 A1 | 8/2014 |

* cited by examiner

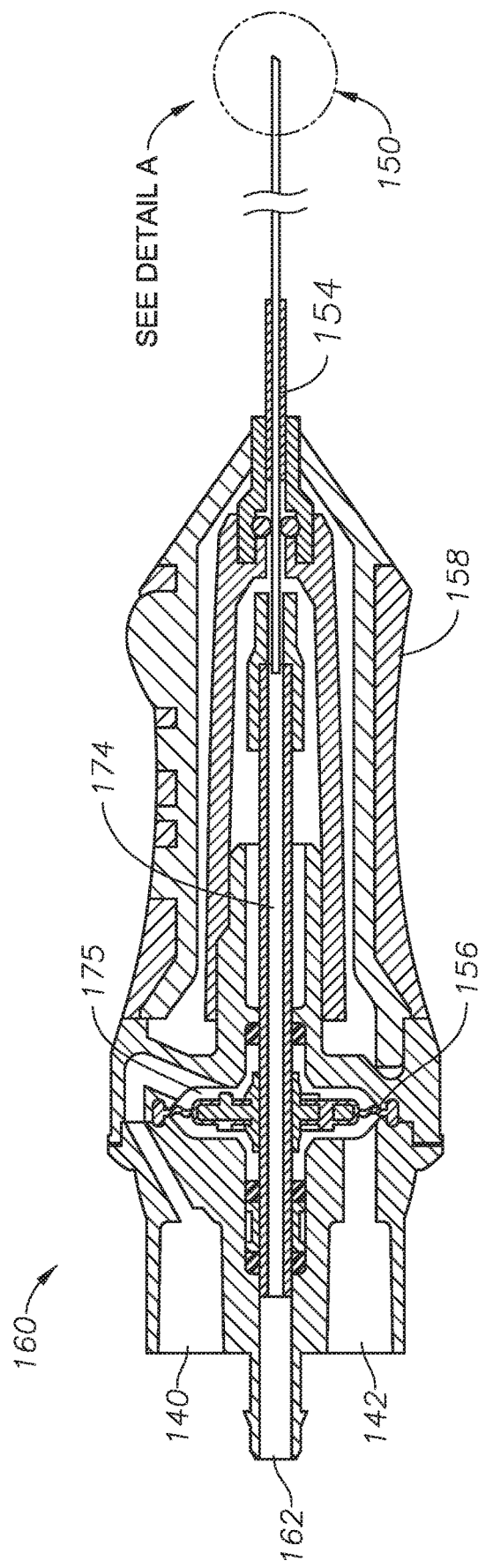
FIG. 3
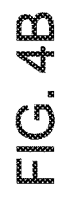
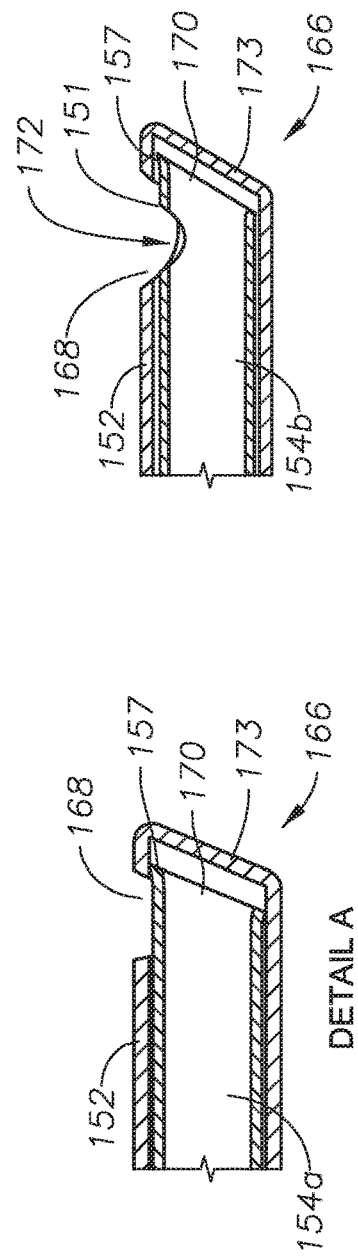
DETAIL A
FIG. 4A
FIG. 4B

Section A-A from FIG. 10

VITRECTOMY PROBE

This application claims the benefit of priority of U.S. Provisional Patent Application Ser. No. 62/521,754 titled "Vitrectomy Probe", filed on Jun. 19, 2017, whose inventors are Jose Luis Lopez, Matthew Douglas McCawley, Brian William McDonell, Timothy C. Ryan, John R. Underwood, Salomon Valencia, and Jack Robert Auld which is hereby incorporated by reference in its entirety as though fully and completely set forth herein.

DESCRIPTION OF THE RELATED ART

Microsurgical procedures frequently require precision cutting and/or removing of various body tissues. For example, certain ophthalmic surgical procedures may require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous may need to be done with great care to avoid traction on the retina, the separation of the retina from the choroid, a retinal tear, or, in the worst case, cutting and removal of the retina itself. In particular, delicate operations such as mobile tissue management (e.g. cutting and removal of vitreous near a detached portion of the retina or a retinal tear), vitreous base dissection, and cutting and removal of membranes may be particularly difficult.

Microsurgical cutting probes used in posterior segment ophthalmic surgery may include a hollow outer cutting member, a hollow inner cutting member arranged coaxially with and movably disposed within the hollow outer cutting member, a port extending radially through the outer cutting member near the distal end of the outer cutting member, and a port extending radially through the inner cutting member near the distal end of the inner cutting member. Vitreous humor and/or membranes may be aspirated into the open port of the outer cutting member and the inner member may be actuated to distally extend the inner cutting member. As the inner cutting member extends distally, cutting surfaces on both the inner and outer cutting members may cooperate to cut the vitreous and/or membranes, and the cut tissue may then be aspirated away through the inner cutting member. Vitreous and/or membranes may then be aspirated into the open ports of both the outer and inner cutting members and the inner member may be actuated to proximally retract the inner cutting member. The inner and outer cutting members may cooperate to again cut vitreous and/or membranes and aspirate the cut tissue away.

A distance between the distal end of the outer cutting member to a nearest cutting edge of the outer port is referred to as the port to tip distance (PTTD). The PTTD may be a function of the over travel of the inner cutting member, the thickness of the outer cutting member cap (at the distal end of the outer cutting member) and the necessary clearance between the inner cutting member and the cap. Typical vitrectomy cutters have a PTTD in a range of 0.009 to 0.025 inches for flat ended vitrectomy probes.

SUMMARY

In various embodiments, a vitrectomy probe may include an outer cutting tube with an outer port side opening and an inner cutting tube positioned inside the outer cutting tube. The inner cutting tube may have an open distal end with a cutting edge. The vitrectomy probe may further include a diaphragm (located inside a drive chamber) coupled to the inner cutting tube. The diaphragm may move back and forth inside the drive chamber as air is alternately supplied (by a pneumatic drive line) and vented on either side of the diaphragm. Movement of the diaphragm may thus cause the inner cutting tube to oscillate inside the outer cutting tube such that the open distal end of the inner cutting tube moves back and forth across the outer port side opening to cut tissue entering the outer port side opening. The inner cutting tube may also have a flat upper edge, perpendicular (or, for example, approximately in a range of 70-110 degrees) to an inner tube longitudinal axis, on the portion of the inner cutting tube that cuts across the outer port side opening. The diaphragm may have an open-stroke side with a first contact surface that contacts an inner drive chamber wall when the inner cutting tube is in a retracted position and a closed-stroke side with a second contact surface that contacts an opposing inner drive chamber wall when the inner cutting tube is in an extended position. The first contact surface may have a material (e.g., silicone or a similar material) with a lower hardness than the second contact surface (which may include, for example, polycarbonate, polysulfone, or a similar material).

In some embodiments, the pneumatic drive line may couple the vitrectomy probe to a surgical console to deliver air to the probe drive chamber from the surgical console. In some embodiments, the pneumatic drive line may include an internal bore with a non-uniform cross-section along a length of the pneumatic drive line. The pneumatic drive line may have a first segment and a second segment (the first segment defining a first passageway having a first diameter and the second segment defining a second passageway having a second diameter). The first diameter may be different than the second diameter.

In some embodiments, the inner cutting tube may have a distal side port with a distal side port cutting edge. As the inner cutting tube retracts inside the outer cutting tube, tissue entering the outer port side opening may also enter the distal side port of the inner cutting tube to be cut by the distal side port cutting edge as the inner cutting tube is retracted in the outer cutting tube.

In some embodiments, an aspiration tubing may be coupled to the inner cutting tube to apply a vacuum to the inner cutting tube. The aspiration tubing may include a first aspiration tubing and a second aspiration tubing coupled to the first aspiration tubing. The second aspiration tubing may be coupled to the vitrectomy probe on a distal end and coupled to the first aspiration tubing on a proximal end. In some embodiments, the second aspiration tubing may have a lower hardness than the first aspiration tubing and may be shorter than the first aspiration tubing.

BRIEF DESCRIPTION OF THE DRAWINGS

The accompanying drawings illustrate embodiments of the devices and methods disclosed herein and, together with the description, serve to explain the principles of the present disclosure.

FIG. 3 is an illustration of an exemplary vitrectomy probe in cross-section operable in accordance with the principles and teachings described herein.

FIG. 4a-b illustrate various vitrectomy probe distal end configurations, according to various embodiments.

It is to be understood that both the foregoing general description and the following detailed description are exemplary and explanatory only and are intended to provide a further explanation of the principles of the present disclosure.

DETAILED DESCRIPTION OF THE EMBODIMENTS

Figure 1:
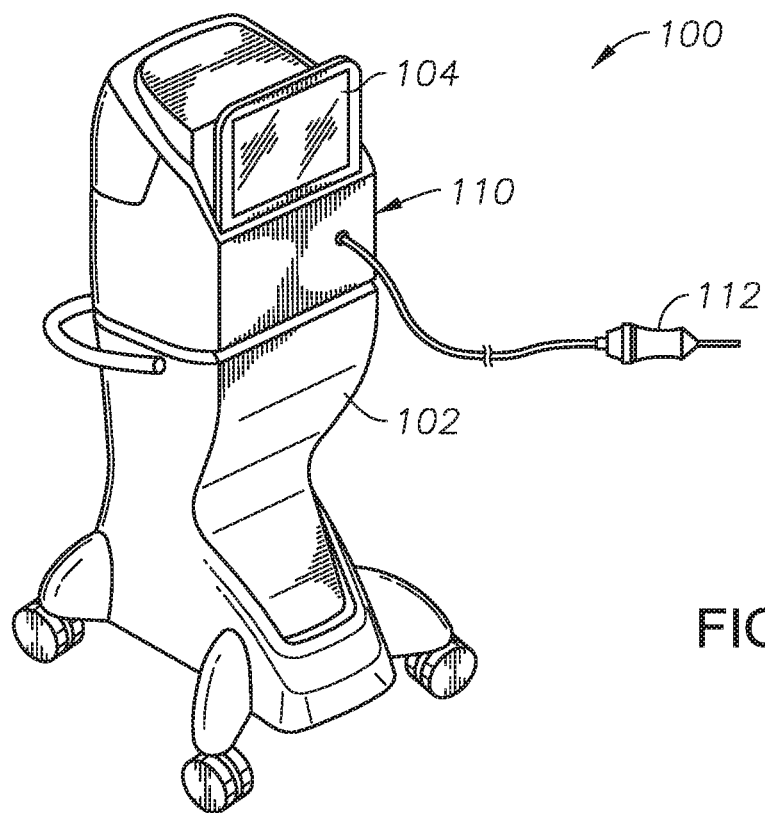
FIG. 1 is an illustration of an exemplary surgical system according to one aspect of the present disclosure consistent with the principles and teachings described herein.

FIG. 1 illustrates a vitrectomy surgical system console, generally designated 100, according to an exemplary embodiment. The surgical console 100 may include a base housing 102 and an associated display screen 104 showing data relating to system operation and performance during a vitrectomy surgical procedure. In an embodiment, the base housing 102 may be mobile, for example including wheels to facilitate movement as necessary. In an alternative embodiment, the base housing 102 may not include wheels. The surgical console 100 may include a vitrectomy probe system 110 that includes a vitrectomy probe 112, as will be discussed in more detail below with respect to subsequent figures.

Figure 2:
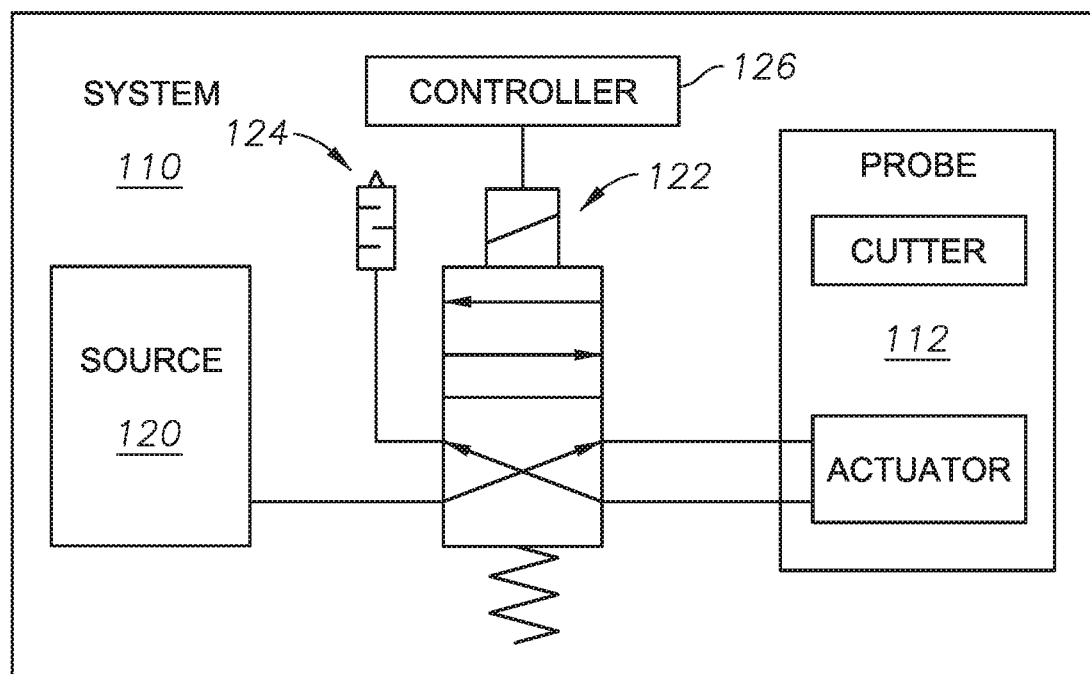
FIG. 2 is a box diagram of aspects of the exemplary surgical system of FIG. 1, according to an embodiment.

FIG. 2 is a schematic of exemplary components of the vitrectomy probe system 110, according to an embodiment. The probe system 110 may include the vitrectomy probe 112, a pneumatic pressure source 120, a probe driver shown as an adjustable directional on-off pneumatic driver 122, a muffler 124, and a controller 126. In an embodiment, the controller 126 may be a processor that includes one or more processing cores capable of performing parallel or sequential operations. Alternatively, the controller 126 may be a dedicated piece of hardware such as an application specific integrated circuit (ASIC), to name just a few examples. The source 120, the driver 122, the muffler 124, and the probe 112 may be in fluid communication with each other along lines representing flow paths or flow lines. The controller 126 may be in electrical communication with the driver 122. In an embodiment, the controller 126 may control operation of both the driver 122 and various aspects of the probe 112, including the frequency of oscillation by way of the actuator as well as a flow rate of fluid to/from the surgical site.

FIG. 3 shows a partial cross-sectional illustration of an exemplary vitrectomy probe, for example the vitrectomy probe 112 introduced in FIGS. 1 and 2. In this example, the vitrectomy probe 112 may be a pneumatically driven probe that operates by receiving pneumatic pressure alternating through first and second ports 140 and 142. The probe 112 may include as its basic components a cutter 150 has an outer cutting tube 152 (also known as a needle), an inner cutting tube 154 shown in a non-sectional side view, and a probe actuator or motor shown here as a reciprocating air driven diaphragm 156, all at least partially encased by a housing 158 in an enclosed drive chamber 175. The housing 158 may include an end piece 160 at the probe proximal end with the first and second air supply ports 140, 142 and one suction port 162 to provide aspiration of materials from the cutter 150.

In an embodiment, the vitrectomy probe system's pneumatic driver 122 (FIG. 2) may be a standard four-way on-off valve. The pneumatic driver 122 may have a solenoid that operates to move the driver to one of the two on-off positions depicted in the example of FIG. 2. Here, the pneumatic driver 122 may be in a position to provide pneumatic pressure to the first port 140 (FIG. 3), and to vent pneumatic pressure from the second port 142 (FIG. 3). In this position, pneumatic pressure may pass from the pressure source 120, through the on-off pneumatic driver 122, and to the first port 140 where the pneumatic pressure provides pneumatic power to the vitrectomy probe 112. At the same time, pneumatic pressure at the second port 142 may pass through the on-off pneumatic driver 122 to the muffler 124 where it is exhausted, for example, to the atmosphere. In the other position, the on-off pneumatic driver 122 may allow pneumatic pressure to pass from the pressure source 120 to the second port 142, where the pneumatic pressure provides pneumatic power to the vitrectomy probe 112. At the same time, pneumatic pressure at the first port 140 may vent through the on-off pneumatic driver 122 to the muffler 124 where it is exhausted to the atmosphere. The on-off pneumatic driver may be configured to receive operating signals from the controller 126.

In operation, pneumatic pressure may be directed alternately from the source 120 to the first and second ports 140, 142 to operate the vitrectomy probe 112. The on-off pneumatic driver 122 may alternate between its two positions very rapidly to alternatingly provide pneumatic pressure to the first and second ports 140, 142. Although shown with a single pneumatic driver 122, other embodiments include two pneumatic drivers, one associated with each of the two ports 140, 142. These embodiments may operate similar to the manner described, with the drivers being configured to independently receive operating signals from the controller 126 (FIG. 2). Yet other arrangements are contemplated.

Returning to FIG. 3, the cutter 150 may extend from the housing 158 and may include a distal end 166, shown in FIG. 4a in greater detail below. The outer cutting tube 152 and the inner cutting tube 154 may both be cylindrical tubes with a hollow bore. As seen in FIGS. 4a-b, the distal ends (needle caps 173) of the outer cutting tube 152 may include beveled (i.e., angled) ends. In some embodiments, the distal ends (needle caps 173) of the outer cutting tubes may be flat. The distal ends of the outer cutting tube 152 may be closed using, for example, spin closed machining, adhesive, welding (e.g., laser welding), etc. For example, the beveled end may be closed by laser welding a pieced onto the angled end. In some embodiments, the inner cutting tube 154 may additionally have an open end, such as depicted in FIGS. 4a-b as a distal port 170.

Generally, the inner cutting tube 154 may oscillate within the outer cutting tube 152 in response to the probe actuator. In an embodiment, the inner cutting tube 154 may be driven by air pressure directed on opposing sides of the diaphragm 156. In one example of operation, if air pressure is increased at the first port 140, the diaphragm 156 may move distally, displacing the inner cutting tube 154 relative to the outer cutting tube 152, thereby moving a first cutting edge 157 on a distal end of the inner cutting tube 154 in the distal direction and cutting tissue. This may cut any vitreous material which may have been aspirated into a tissue-receiving outer port 168 of the outer cutting tube 152. In some embodiments, the first cutting edge 157 may be formed on a flared distal end of the inner cutting tube 154 (as illustrated in FIGS. 4a-b). In some embodiments, the distal end of the inner cutting tube 154 may not be flared. The vitreous may be aspirated through a distal opening 170 of the inner cutting tube 154. In some embodiments, the vitreous may also be aspirated through distal port 172 in the side of inner cutting tube 154b. "154a" used in the Figures to depict inner cutting tube with no side distal port 172, and "154b" used in the Figures to depict inner cutting tube with a side distal port 172 ("154a" and "154b" are generally referred to as "154" in the drawings and the specification when the expressed detail may apply to both "154a" and "154b"). Venting the pressure at the first port 140 and increasing the pressure at the second port 142 may move the diaphragm 156 proximally, moving a second cutting edge 151 facing a proximal direction near the distal end of the inner cutting tube 154b in the proximal direction, cutting any vitreous material which may have entered the outer port 168 of the outer cutting tube 152 and the side distal port 172 of the inner cutting tube 154b while at least partially aligned.

Figure 5:
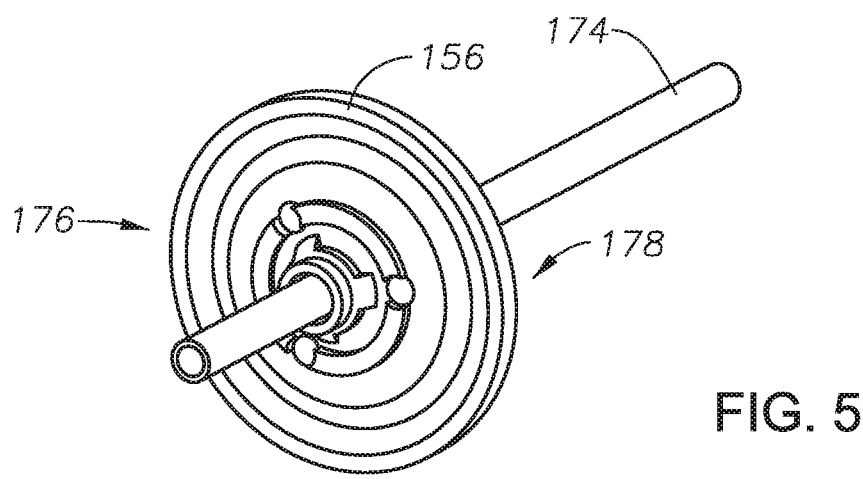
FIG. 5 illustrates a diaphragm and drive shaft, according to an embodiment.

FIG. 5 illustrates the diaphragm 156 and drive shaft 174, according to one embodiment. The diaphragm 156 may include an open-stroke side 176 (i.e., the side of the diaphragm 156 making contact with a proximal enclosed drive chamber wall 181 (see FIG. 7) when the inner cutting tube 154 is in a retracted (proximal-most) position with respect to the outer cutting tube 152). The diaphragm 156 may also include a closed-stroke side 178 (i.e., the side of the diaphragm 156 making contact with a distal enclosed drive chamber wall 182 when the inner cutting tube 154 is in an extended (distal-most) position with respect to the outer cutting tube 152).

Figure 6A:
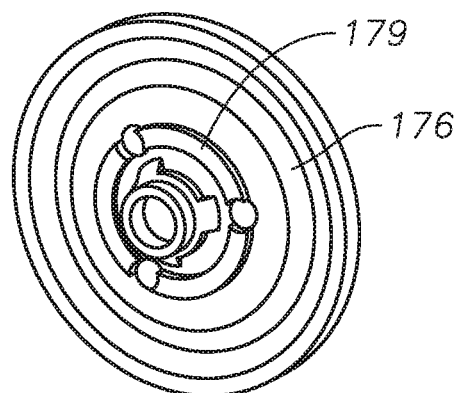
FIGS. 6a-b illustrate opposing sides of a diaphragm, according to an embodiment.
Figure 6B:
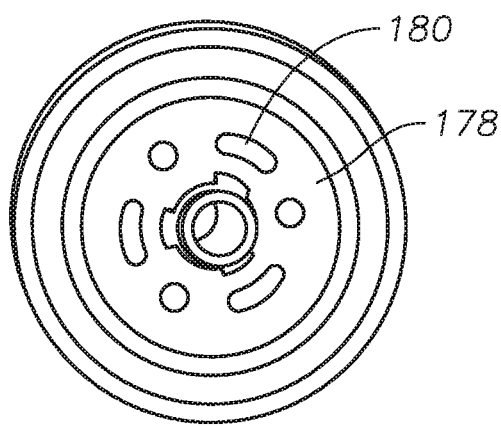

As seen in FIGS. 6a-b, in some embodiments, the diaphragm 156 may include a first contact surface (e.g., proximal stops 179) and a second contact surface (e.g., distal stops 180) on opposing sides of the diaphragm 156. In some embodiments, the proximal/distal stops 179/180 may come in contact with their respective drive chamber walls 181/182. For example, proximal stops 179 may make contact with the proximal enclosed drive chamber wall 181 when the inner cutting tube 154 is in a retracted/proximal most position. Distal stops 180 may make contact with the distal enclosed drive chamber wall 182 when the inner cutting tube 154 is in an extended/distal most position. The stops 179/180 may be made of a rigid material (e.g., polycarbonate, polysulfone, or a similar material) or a relatively soft material (e.g., silicone or a similar material). In some embodiments, the stops 179/180 may be made of the same material. In some embodiments, the stops may be made of different materials. For example, proximal stops 179 may be made of a soft material (e.g., silicone or a similar material) and distal stops 180 may be made of a rigid material (e.g., polycarbonate, polysulfone, or a similar material). In another embodiment, proximal stops 179 may be made of a rigid material (e.g., polycarbonate, polysulfone, or a similar material) and distal stops 180 may be made of a soft material (e.g., silicone or a similar material). In some embodiments, the softer material may reduce noise from the impact of the contact surfaces of the diaphragm 156 against the chamber walls 181/182. Rigid material may be used to provide a more consistent stop (e.g., the distal stops 180 may be made of a rigid material to insure the inner cutting tube 154 stops short of a distal end of the outer cutting tube 152. By making the proximal stop of a relatively soft material and the distal stops of a rigid material, the probe may have a quieter operation and keep a reliable stopping distance between the inner and outer cutting tubes.

Figure 7:
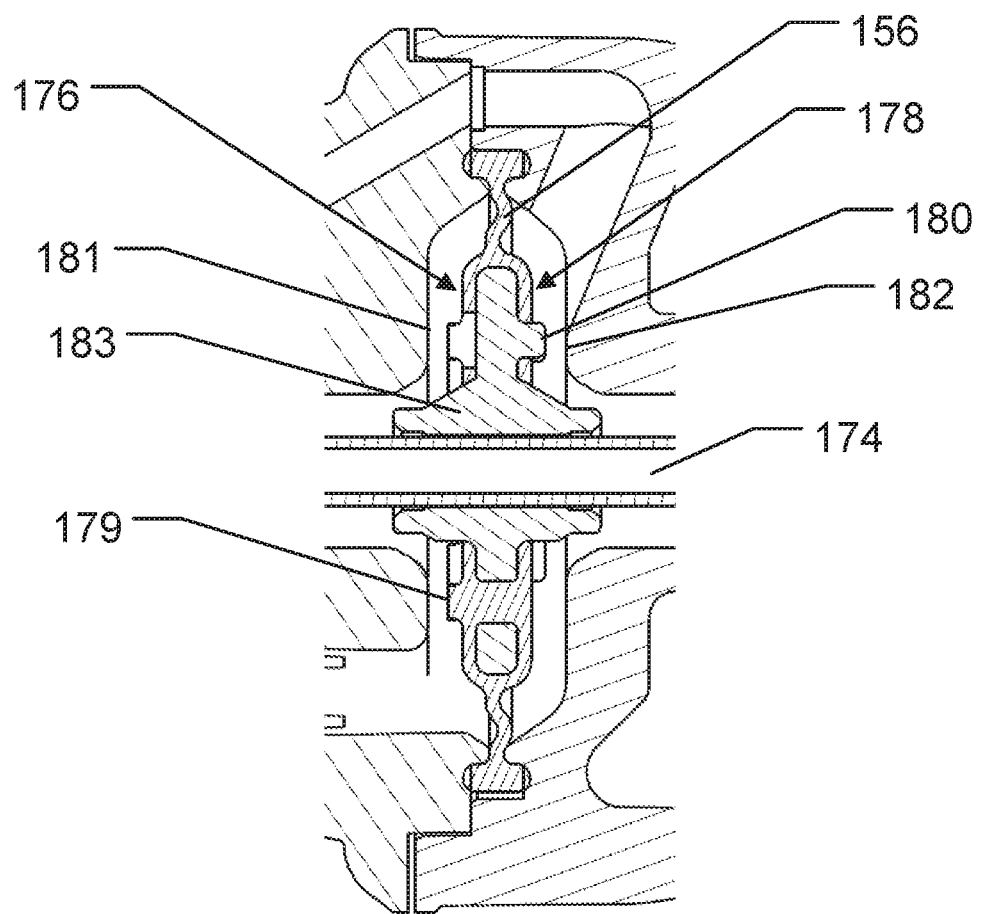
FIG. 7 illustrates a cross section of the diaphragm chamber in a vitrectomy probe, according to an embodiment.

While three distal stops 180 are shown, other numbers of stops may be used (e.g., 1 stop or more such as 10 stops distributed on the contact surface) (even more stops may be used). While the distal stops 180 are shown as elliptical, other shapes of stops 180 are also possible (e.g., rectangular). While three proximal stops 179 are shown, other numbers of stops may be used (e.g., 1 stop or more such as 10 stops distributed on the contact surface) (even more stops may be used). While the proximal stops 179 are shown as three arc segments of a circular rise on the diaphragm 156, other shapes of stops 179 are also possible (e.g., rectangular). In some embodiments, the diaphragm 156 may be made of the same material as one or more of the stops 179/180. For example, the distal stops 180 may be extensions of the diaphragm material while the proximal stops 179 may include material coupled to the diaphragm (e.g., silicone overmolded, attached through adhesive, snapped onto, etc. the diaphragm 156). As seen in FIG. 7, in some embodiments, the proximal stops 179 may be extensions of the diaphragm material while the distal stops 180 may include material coupled on the diaphragm 156. For example, the diaphragm 156 made be made of a silicone material that has the proximal stops formed thereon with rigid distal stops coupled to the diaphragm 156 (e.g., overmolded onto the silicone (or the silicone overmolded onto the rigid distal stops), attached through adhesive, snapping onto the silicone, etc.) As seen in FIG. 7, the distal stops 180 and a central receiving portion 183 (receiving the drive shaft 174) may be made of a rigid material (such as polycarbonate, polysulfone, or a similar material) and the diaphragm 156 (e.g., made of silicone or a similar material) may include silicone portions for the proximal stops 179 that are molded onto the rigid material to form an integrated piece. The circular recesses shown near the proximal stops 179 may be used as part of the molding process. In some embodiments, the proximal stops 179 may be a continuous circular rise on the diaphragm 156.

Figure 8:
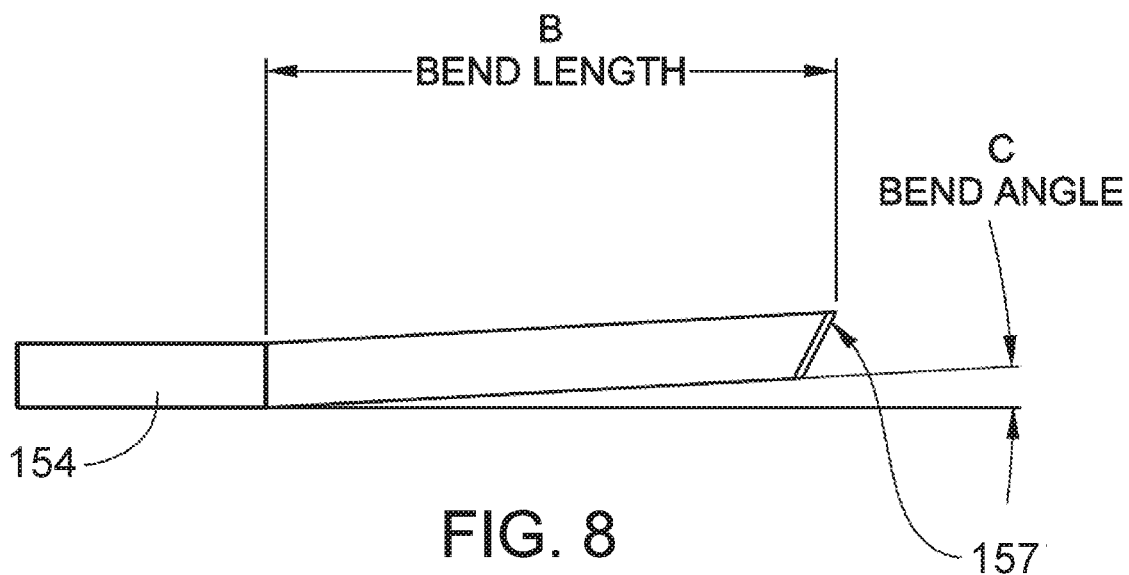
FIG. 8 illustrates an inner cutting tube bend, according to an embodiment.

FIG. 8 illustrates an inner cutting tube 154 bend, according to an embodiment. In some embodiments, the inner cutting tube 154 may have a slight bend to bias the first cutting edge 157 against the inside wall of the outer cutting tube 152 to insure a cutting action on the vitreous entering the port 168. In some embodiments, the angle may vary according to the size of the outer cutting tube 152. For example, for 23 gauge outer cutting tubes 152, the bend angle (C) may be approximately 3.5 degrees with a bend length (B) (i.e., distance from the distal end of the inner cutting tube 154 to the bend) of approximately 0.110 inches. Other bend angles (C) and bend lengths (B) for 23 gauge outer cutting tubes are also contemplated (e.g., a bend angle (C) approximately in a range of 2.0 degrees to 5.0 degrees or approximately in a range of 3.0 to 4.0 degrees and a bend length (B) approximately in a range of 0.065 to 0.15 inches or approximately in a range of 0.1 to 0.13 inches). As another example, for 25 gauge outer cutting tubes 152, the bend angle (C) may be approximately 4.7 degrees with a bend length (B) of approximately 0.060 inches. Other bend angles (C) and bend lengths (B) for 25 gauge outer cutting tubes are also contemplated (e.g., a bend angle (C) approximately in a range of 2.8 degrees to 6.5 degrees or approximately in a range of 4.0 to 5.5 degrees and a bend length (B) approximately in a range of 0.035 to 0.15 inches or approximately in a range of 0.05 to 0.07 inches). As a further example, for 27 gauge outer cutting tubes 152, the bend angle (C) may be approximately 4.3 degrees with a bend length (B) of approximately 0.050 inches. Other bend angles (C) and bend lengths (B) for 27 gauge outer cutting tubes are also contemplated (e.g., a bend angle (C) approximately in a range of 2.6 degrees to 6.0 degrees or approximately in a range of 3.7 to 4.9 degrees and a bend length (B) approximately in a range of 0.03 to 0.07 inches or approximately in a range of 0.04 to 0.06 inches). As another example, for a dual port probe (e.g., see FIG. 4b), the bend angle (C) may be approximately 3.2 degrees and the bend length (B) may be approximately 0.050 inches. Other bend angles (C) and bend lengths (B) for dual port probes are also contemplated (e.g., a bend angle (C) approximately in a range of 1.9 degrees to 4.5 degrees or approximately in a range of 2.7 to 3.7 degrees and a bend length (B) approximately in a range of 0.03 to 0.07 inches or approximately in a range of 0.04 to 0.06 inches).

While example dimensions/measurements and dimensions/measurement ranges are provided throughout the application, these dimensions/measurements should not be construed as limiting as they only present a possible set of dimensions/measurements. Other dimensions/measurements are also contemplated.

Figure 9:
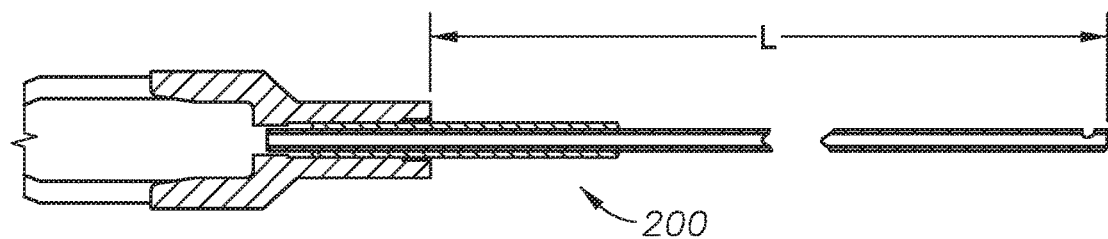
FIG. 9 illustrates a stiffener on the outer cutting tube, according to an embodiment.

As shown in FIG. 9, the outer cutting tube 152 may have support from a stiffener 200 extending around the base of the outer cutting tube 152 at the probe body. In some embodiments, the probe may not include a stiffener 200. The length (L) of the outer cutting tube from the probe body to the distal end may vary according to the size of the outer cutting tube 152. For example, for 23 or 25 gauge outer cutting tubes 152, the length (L) may be approximately 1.25 inches. Other lengths (L) are also contemplated (e.g., length (L) for a 23 or 25 gauge outer cutting tube may be approximately in a range of 0.75 to 1.75 inches or approximately in a range of 1.1 to 1.4 inches). The 23 and 25 gauge outer cutting tubes may not include stiffeners 200 (or they may include stiffeners 200). In an embodiment of the 25 gauge outer cutting tube length with a stiffener 200, the length (L) may be approximately 1.063 inches. Other lengths (L) are also contemplated (e.g., length (L) for a 25 gauge outer cutting tube with a stiffener may be approximately in a range of 0.65 to 1.5 inches or approximately in a range of 0.9 to 1.2 inches). As a further example, for 27 gauge outer cutting tubes 152 with stiffeners 200, the length (L) may be approxi-mately 1.023 inches. Other lengths (L) are also contemplated (e.g., length (L) for a 27 gauge outer cutting tube with a stiffener may be approximately in a range of 0.6 to 1.4 inches or approximately in a range of 0.85 to 1.2 inches). Other lengths (L) are also possible. For example, length (L) for all gauges with or without a stiffeners may be approximately in a range of 0.1 to 3 inches.

Figure 10:
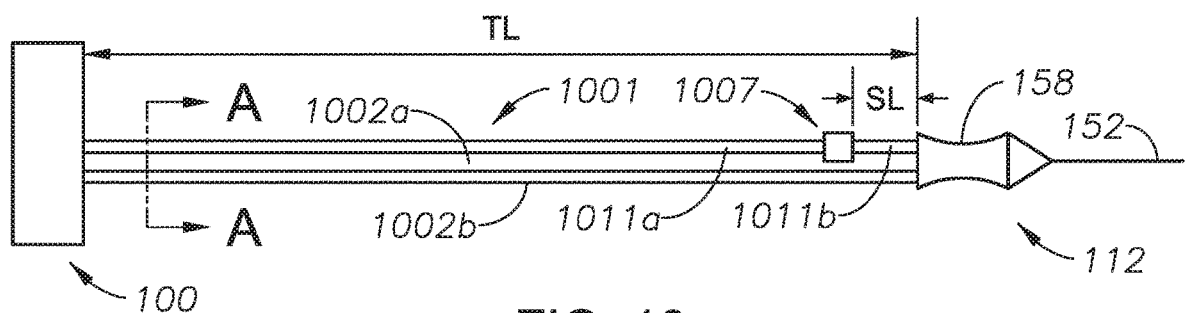
FIG. 10 illustrates tubing segments coupling the probe to a surgical console, according to an embodiment.

FIG. 10 illustrates tubing segments coupling the probe 112 to a surgical console 100, according to an embodiment. As seen in FIG. 10, in some embodiments, the probe 112 may be coupled to the surgical console 100 by three lines (an aspiration tube 1001 and two pneumatic tubes 1002a-b). The pneumatic tubes 1002a-b may include a plastic tubing extending from the console 100. In some embodiments, the pneumatic tubes 1002a-b may have a hardness approximately in a range of 50-120 Shore A hardness (e.g., a hardness of 80 Shore A). Other hardnesses are also contemplated. In some embodiments, the pneumatic tubing 1002a-b may each have a length TL of 84 inches. Other lengths are also contemplated (e.g., the length TL may be approximately in a range of 50 to 120 inches or approximately in a range of 70 to 100 inches).

In some embodiments, the aspiration tube 1001 may include two or more tubing segments 1011a-b. The aspiration tubing segments 1011a-b may be coupled together through a tubing connector 1007. The connector 1007 may connect to each tubing segment through a friction fit (e.g., ends of the tubing segments 1011a-b may slide over respective receiving male connector segments and stay secured through friction between the inner surface of the tubing and the male connector segments). Other attachments are also contemplated (e.g., adhesive, crimping, etc.) In some embodiments, the tubing segments 1011a-b may be a single continuous tube that has properties that transition at a point along the tubing or gradually along at least a portion of the tubing. In some embodiments, the aspiration tubing segments 1011a-b may have different lengths. For example, the tubing segment 1011a from the console 100 to the connector 1007 may be substantially longer than the tubing segment 1011b from the handpiece 112. As one example of relative lengths, the aspiration tubing segment 1011a from the console 100 to the connector 1007 may have a length of approximately 79 inches and the aspiration tubing segment 1011b from the connector 1007 to the handpiece 112 may have a length SL of approximately 5 inches. Other lengths are also contemplated. For example, the aspiration tubing segment 1011a from the connector 1007 to the console 100 may have a length approximately in a range of 45 to 110 inches or approximately in a range of 65 to 95 inches. The aspiration tubing segment 1011b from the connector 1007 to the handpiece 112 may have a length SL approximately in a range of 3 to 7 inches or approximately in a range of 4 to 6 inches. In some embodiments, the aspiration tubing segments 1011a-b may have different hardnesses. For example, the longer aspiration tubing segment 1011a from the console 100 to the connector 1007 may have a higher hardness than the shorter aspiration tubing segment 1011b from the connector 1007 to the handpiece. For example, in one embodiment, the hardness of the longer aspiration tubing segment 1011a may be approximately 80 Shore A hardness and the hardness of the shorter aspiration tubing segment 1011b may be approximately 40 Shore A hardness. Other hardnesses are also contemplated. For example, the hardness of the longer aspiration tubing segment 1011a may be approximately in a range of 50 to 115 Shore A hardness or approximately in a range of 70 to 95 Shore A hardness. The hardness of the shorter aspiration tubing segment 1011b may be approximately in a range of 25 to 55 Shore A hardness or approximately in a range of 35 to 45 Shore A hardness. In some embodiments, the shorter, lower hardness aspiration tubing segment may also make the handpiece 112 easier to handle by the surgeon (versus a handpiece coupled through a high hardness tubing). The lower hardness tubing may be more flexible than the higher hardness tubing.

Figure 11:
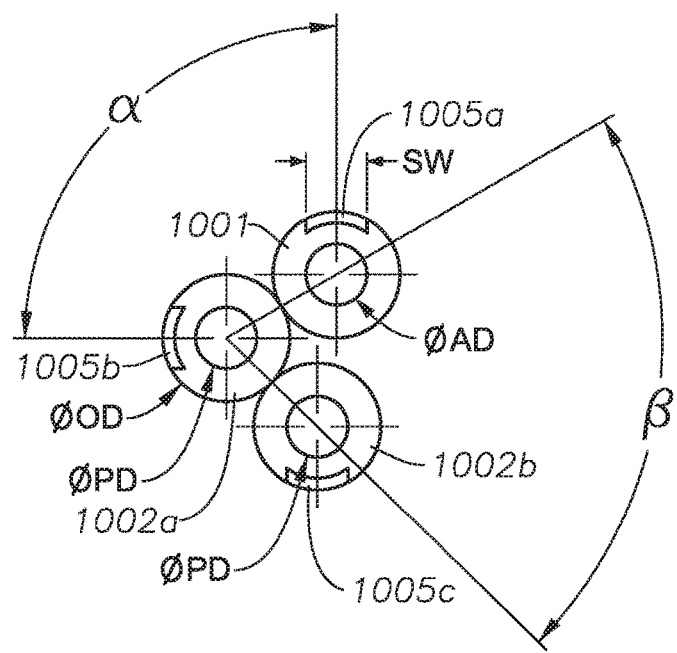
FIG. 11 illustrates a cross section of the pneumatic and aspiration tubing segments, according to an embodiment.

As seen in FIG. 11, the pneumatic tubing 1002a-b and aspiration tubing 1001 may be coupled together through at least a portion of their lengths. For example, the tubing may be coupled together through being coextruded or through an adhesive along the lengths of tubings to hold them together. In some embodiments, an angle α between centerpoints of the coupled pneumatic tubing 1002a-b may be approximately 90 degrees as shown in FIG. 11. Other values of α are also contemplated (e.g., approximately in a range of 55 degrees to 125 degrees or approximately in a range of 75 to 100 degrees). In some embodiments, an angle β between the centerpoints of the coupled pneumatic tubing 1002a-b and aspiration tubing 1001 may be approximately 75 degrees as shown in FIG. 11. Other values of β are also contemplated (e.g., approximately in a range of 45 degrees to 105 degrees or approximately in a range of 65 to 85 degrees). In some embodiments, the pneumatic tubing 1002a-b and aspiration tubing 1001 may not be coupled together along their lengths.

In some embodiments, the pneumatic tubing 1002a-b and aspiration tubing 1001 may have indicators on the tubing to indicate the tubing type. For example, stripes 1005a-b may be included along at least a portion of the tubing lengths. In some embodiments, a blue stripe 1005a may indicate an aspiration tubing 1001. A black stripe 1005b may be used to indicate a first pneumatic tubing 1002a and a grey stripe 1005c may be used to indicate the second pneumatic tubing 1002b. In some embodiments, the stripes may be approximately 0.060 inches in width SW. Other widths SW are also contemplated (e.g., approximately in a range of 0.035 to 0.085 inches or approximately in a range of 0.05 to 0.07 inches). Other indicators are also contemplated.

As further seen in FIG. 11, the inner diameter ØPD of the pneumatic tubing 1002a-b may be approximately 0.075 inches. Other diameters are also contemplated (e.g., approximately in a range of 0.045 to 0.10 inches or approximately in a range of 0.065 to 0.085 inches). In some embodiments, the inner diameter ØAD of the aspiration tubing 1001 may be approximately 0.06 inches. Other diameters are also contemplated (e.g., approximately in a range of 0.035 to 0.085 inches or approximately in a range of 0.05 to 0.07 inches). In some embodiments, the pneumatic tubing 1002a-b and aspiration tubing 1001 may all have the same outer diameter ØOD of approximately 0.125 inches. Other outer diameters ØOD are also contemplated (e.g., approximately in a range of 0.075 to 0.18 inches or approximately in a range of 0.10 to 0.15 inches). In some embodiments, the pneumatic tubing 1002a-b or aspiration tubing 1001 may have different diameters than the other of the pneumatic tubing 1002a-b or aspiration tubing 1001.

Figure 12A:
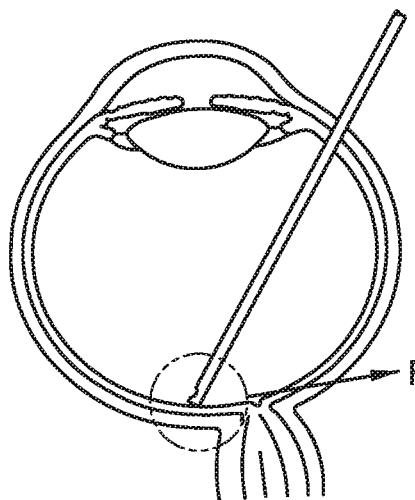
FIGS. 12a-c illustrate vitrectomy probe distal ends, according to various embodiments.
Figure 12B:
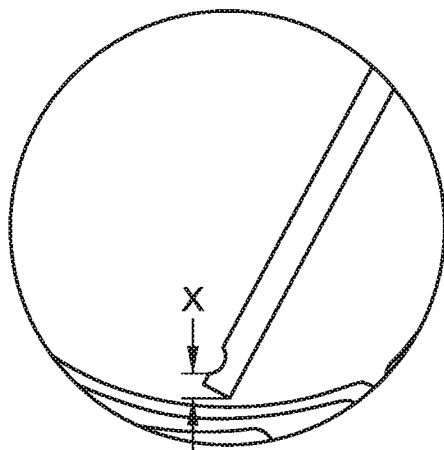
Figure 12C:
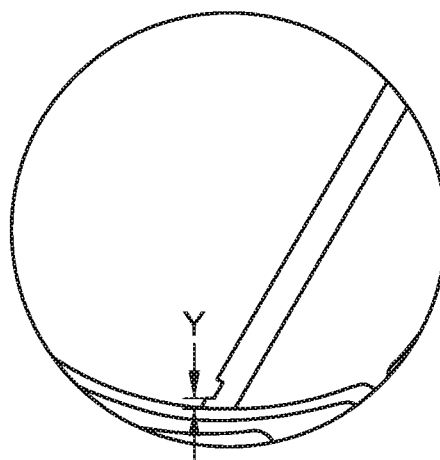

FIGS. 12a-c illustrate vitrectomy probe distal ends, according to various embodiments. FIG. 12a illustrates a cross section of the eye with a vitrectomy probe. FIG. 12b illustrates a close-up of a flat distal tip vitrectomy probe near the retina (e.g., at a port edge tip to retinal (PTRD) distance X from the retina). The PTRD is the shortest distance between the port edge and the retina. As seen in FIG. 12c, the user can position the port closer (e.g., a PTRD distance Y where Y<X) to the retina of the eye if the distal end of the vitrectomy probe is beveled. For example, X may be 0.018 inches while Y may be 0.008 inches. Other X and Y values are also contemplated. When using the vitrectomy probe, the user may want to remove vitreous as close to the retina as possible without cutting the retina itself. The beveled tip may allow shaving or dissection of tissue/membranes near the retina. The beveled tip may also allow the user to lift and pick membranes without having to switch to another instrument.

Figure 13A:
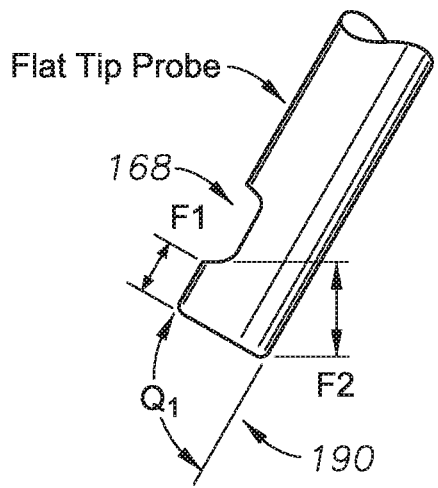
FIGS. 13a-b illustrate measurements for the outer cutting tube of the vitrectomy probe, according to various embodiments.
Figure 13B:
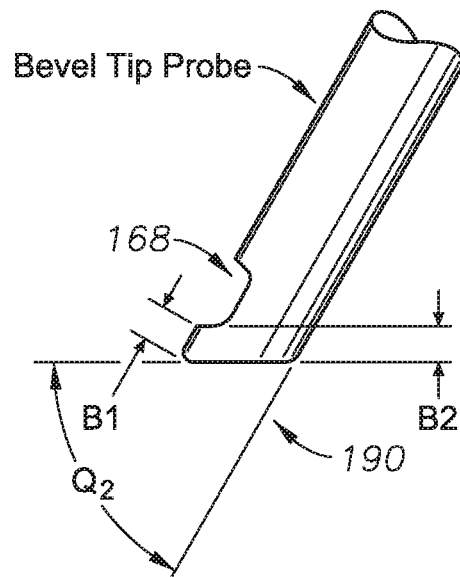

FIGS. 13a-b illustrate some measurements for the outer cutting tube 152 of the vitrectomy probe, according to various embodiments. As seen in FIG. 13a, in some embodiments of the flat tip (where angle Q1, from a distal end surface of the outer cutting tube 152 to an extended back surface line 190 of the outer cutting tube that is opposite the outer port side opening, is 90 degrees), the port edge to distal probe tip (PTTD) measurement F1 may be approximately 0.009 inches for 23, 25, and 27 gauge probes. Other PTTD measurements F1 are also contemplated. For example, PTTD measurement F1 may be approximately in a range of 0.003 to 0.015 inches, approximately in a range of 0.003 to 0.0085 inches, approximately in a range of 0.005 to 0.025 inches, or approximately in a range of 0.008 to 0.010 inches. In some embodiments, the PTTD measurement F1 may be a function of over travel of the inner cutting tube 154 (i.e., how far the inner cutting tube 154 travels inside the outer cutting tube 152 during the distal most portion of the inner cutting tube 154 movement), thickness of the needle cap 173, and clearance between the inner cutting tube 154 and the cap 173 (i.e., the distance between the distal most end of the inner cutting tube 154 and the cap 173 at the distal most point of the inner cutter tube's travel inside the outer cutting tube 152). In some embodiments, the port edge tip to retinal distance (PTRD) F2 for the flat tip may be approximately 0.021 inches for a 23 gauge probe, approximately 0.018 inches for a 25 gauge probe, and approximately 0.016 inches for a 27 gauge probe. Other PTRD distances for flat tips F2 are also contemplated (e.g., F2 may be approximately in a range of 0.01 to 0.03 inches for the various gauge probes). As seen in FIG. 13b, in some embodiments of the beveled tip, the PTRD for the beveled tip B2 (at an angle Q2, from a distal end surface of the outer cutting tube 152 to an extended back surface line 190 of the outer cutting tube that is opposite the outer port side opening, is approximately 60 degrees) may be approximately 0.009 inches for a 23 gauge probe, approximately 0.008 inches for a 25 gauge probe, and approximately 0.007 inches for a 27 gauge probe. Other PTRD measurements B2 are also contemplated (for example, angle Q2 may be approximately in a range of 20 to 80 degrees with a PTRD measurement B1 approximately in a range of 0.005 inches to 0.010 inches for 23, 25, and 27 gauge probes). Other PTRD measurements B2 are also contemplated (e.g., PTRD may be approximately in a range of 0.003 to 0.015 inches, approximately in a range of 0.003 to 0.0085 inches, approximately in a range of 0.005 to 0.025 inches, or approximately in a range of 0.008 to 0.010 inches for angle Q2 approximately in a range of 20 to 80 degrees). In some embodiments, an angle Q2 of approximately 60 degrees may result in the PTTD of the probe being approximately equal to the PTRD.

Figure 14A:
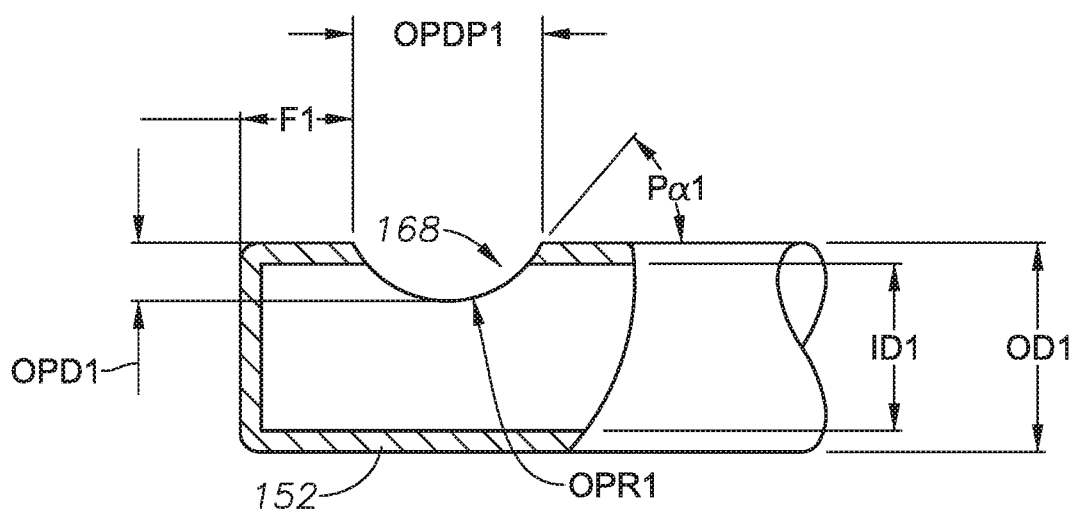
FIGS. 14a-c illustrate measurements for the outer cutting tube and inner cutting tube of the vitrectomy probe, according to an embodiment.
Figure 14B:
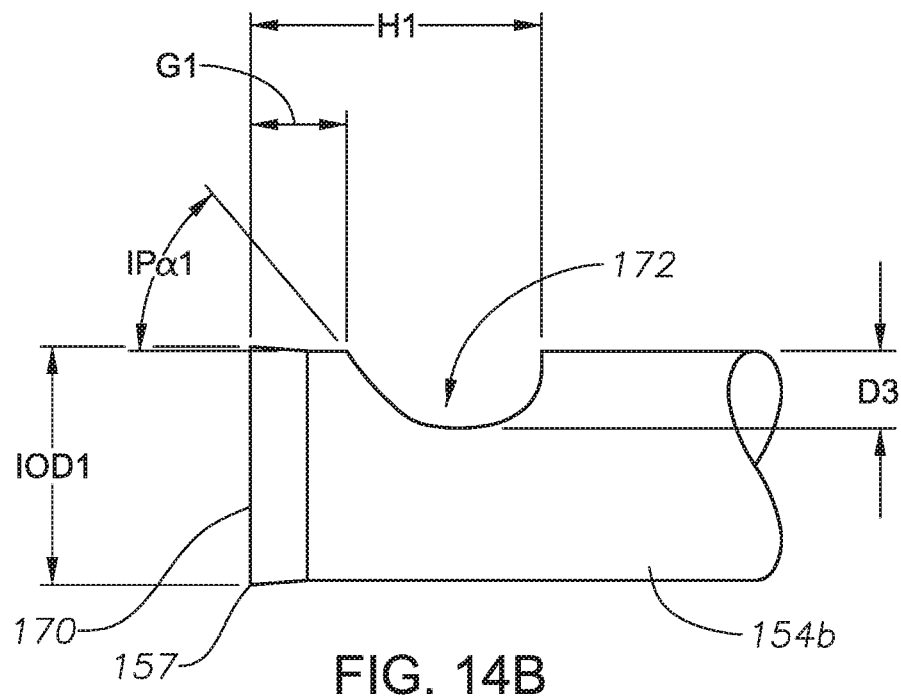
Figure 14C:
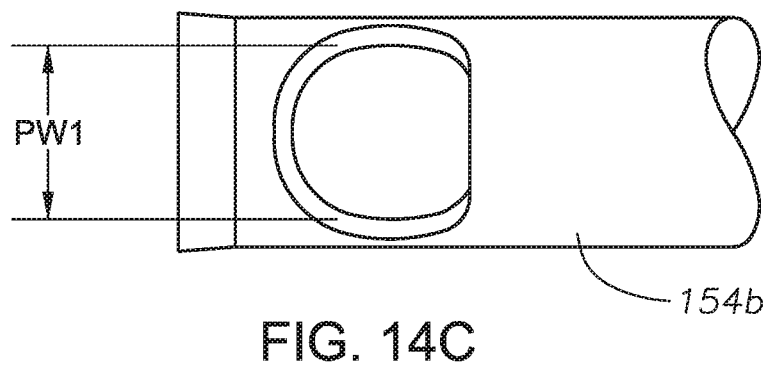

FIGS. 14a-c illustrate some measurements for the outer cutting tube 152 and inner cutting tube 154b of the vitrectomy probe, according to various embodiments. The outer port side opening 168 may have an approximate diameter OPDP1 of 0.015 inches. Other diameters are also contemplated (e.g., approximately in a range of 0.009 to 0.02 inches or approximately in a range of 0.013 to 0.017 inches). The port opening 168 may be circular, elliptical, or some other shape. The outer port opening depth OPD1 may be approximately 0.0045 in. Other outer port opening depths OPD1 are also contemplated (e.g., approximately in a range of 0.0027 to 0.063 inches or approximately in a range of 0.0038 to 0.0052 inches). The outer port radius OPR1 may be approximately 0.008 inches. Other outer port radius OPR1 are also contemplated (e.g., approximately in a range of 0.0048 to 0.0112 inches or approximately in a range of 0.0068 to 0.0092 inches). The proximal port edge angle P$\alpha$1 may be approximately 50 degrees. Other proximal port edge angles P$\alpha$1 are also contemplated (e.g., approximately in a range of 30 to 70 degrees or approximately in a range of 40 to 60 degrees). The inner diameter ID1 of the outer cutting tube 152 may be approximately 0.0131 inches. Other inner diameters ID1 are also contemplated (e.g., approximately in a range of 0.0079 to 0.018 inches or approximately in a range of 0.011 to 0.015 inches). The outer diameter OD1 of the outer cutting tube 152 may be approximately 0.0165 inches. Other outer diameters OD1 are also contemplated (e.g., approximately in a range of 0.010 to 0.023 inches or approximately in a range of 0.014 to 0.019 inches).

As seen in FIG. 14b, a port depth D3 of the distal port 172 of the inner cutting tube 154b may be approximately 0.004 inches. Other port depths D3 are also contemplated (e.g., approximately in a range of 0.0024 to 0.0056 inches or approximately in a range of 0.034 to 0.0046 inches). An inner cutter inner diameter IOD1 of the inner cutting tube 154b may be approximately 0.0127 inches with a flare out to 0.0130 inches at the first cutting edge 157. Other inner cutter inner diameters IOD1 are also contemplated (e.g., approximately in a range of 0.0076 to 0.018 inches or approximately in a range of 0.011 to 0.015 inches). Other flare outs to the first cutting edge 157 are also contemplated (e.g., approximately in a range of 0.0078 to 0.02 inches or approximately in a range of 0.010 to 0.014 inches). The inner tube distal port to edge measurement G1 may be approximately 0.005 inches. In another embodiment, the inner tube port to edge measurement G1 may be approximately 0.006 inches. Other inner port to edge measurements G1 are also possible (e.g., G1 may be approximately in a range of 0.003 inches to 0.012 inches or approximately in a range of 0.003 to 0.007 inches or approximately in a range of 0.004 to 0.006 inches). The inner tube proximal port to edge measurement H1 may be approximately 0.0155 inches. Other inner tube proximal port to edge measurements H1 are also contemplated (e.g., approximately in a range of 0.0093 to 0.022 inches or approximately in a range of 0.013 to 0.018 inches). The inner port edge angle IP$\alpha$1 may be approximately 50 degrees. Other port edge angles $\alpha$1 are also contemplated (e.g., approximately in a range of 30 to 70 degrees or approximately in a range of 40 to 60 degrees). As seen in FIG. 14c, the inner cutting tube port width PW1 may be approximately 0.009 inches. Other inner cutting tube port widths PW1 are also contemplated (e.g., approximately in a range of 0.0054 to 0.013 inches or approximately in a range of 0.0077 to 0.011 inches).

FIGS. 15a-d illustrate measurements for the outer cutting tube 152 and inner cutting tube 154c of the vitrectomy probe 112, according to an embodiment of the inner tube having a flattened edge feature 185. The dimensions not specified in FIGS. 15a-d may have the same value or value ranges as their counterpart dimensions specified in FIGS. 14a-c. The port edge to distal probe tip (PTTD) measurement F2 may be approximately 0.0098 inches for 23, 25, and 27 gauge probes. Other PTTD measurements F2 are also contemplated. For example, PTTD measurement F2 may be approximately in a range of 0.0058 to 0.0137 inches, approximately in a range of 0.0083 to 0.011 inches, approximately in a range of 0.003 to 0.015 inches, approximately in a range of 0.003 to 0.0085 inches, approximately in a range of 0.005 to 0.025 inches, or approximately in a range of 0.008 to 0.010 inches. The port opening 168 may be circular, elliptical, or some other shape. The proximal port edge angle OP$\alpha$2 may be approximately 50 degrees. Other proximal port edge angles OP$\alpha$1 are also contemplated (e.g., approximately in a range of 30 to 70 degrees or approximately in a range of 40 to 60 degrees). The distal port edge angle OD$\alpha$2 may be approximately 45 degrees. Other proximal port edge angles OD$\alpha$2 are also contemplated (e.g., approximately in a range of 25 to 65 degrees or approximately in a range of 35 to 55 degrees). The outer tube upper edge radius UER2 may be approximately 0.002 inches. Other outer tube upper edge radius UER2 are also contemplated (e.g., approximately in a range of 0.0012 to 0.0028 degrees or approximately in a range of 0.0017 to 0.0023 degrees). The thickness of the distal outer tube wall T2 may be approximately 0.0022 inches. Other thicknesses T2 are also contemplated (e.g., approximately in a range of 0.0013 to 0.0031 degrees or approximately in a range of 0.0018 to 0.0025 degrees). The outer tube diagonal distance J2 may be approximately 0.010 inches. Other outer tube diagonal distances J2 are also contemplated (e.g., approximately in a range of 0.006 to 0.014 degrees or approximately in a range of 0.0085 to 0.0115 degrees). The inner diameter ID2 of the outer cutting tube 152 may be approximately 0.0131 inches. Other inner diameters ID2 are also contemplated (e.g., approximately in a range of 0.0079 to 0.018 inches or approximately in a range of 0.011 to 0.015 inches). The outer diameter OD2 of the outer cutting tube 152 may be approximately 0.0165 inches. Other outer diameters OD2 are also contemplated (e.g., approximately in a range of 0.010 to 0.023 inches or approximately in a range of 0.014 to 0.019 inches).

Figure 15A:
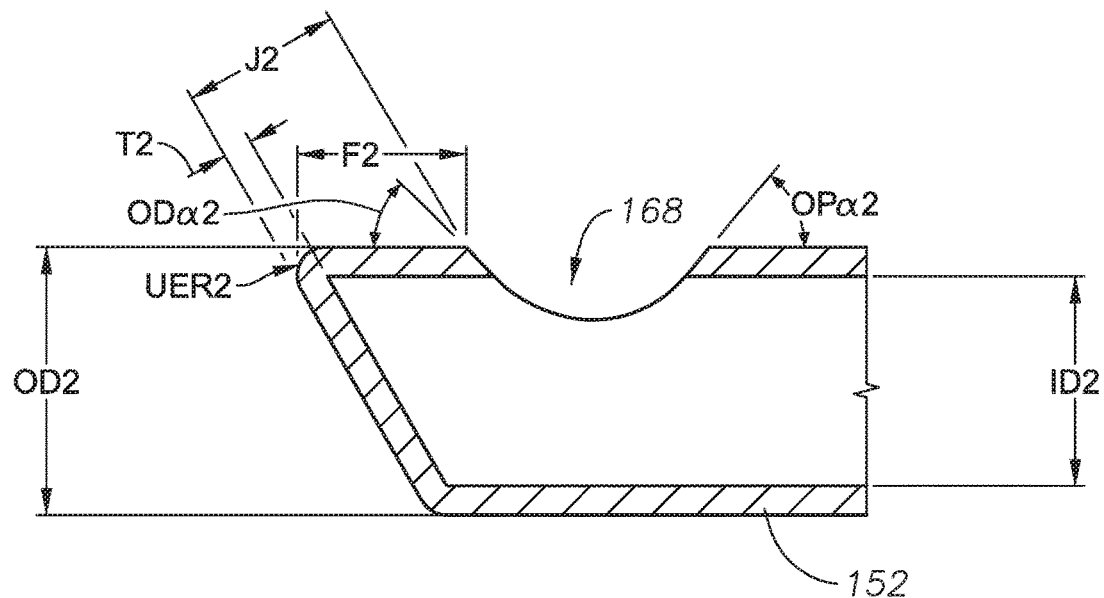
FIGS. 15a-d illustrate measurements for the outer cutting tube and inner cutting tube of the vitrectomy probe, according to an embodiment of the inner tube having a flattened edge feature.
Figure 15B:
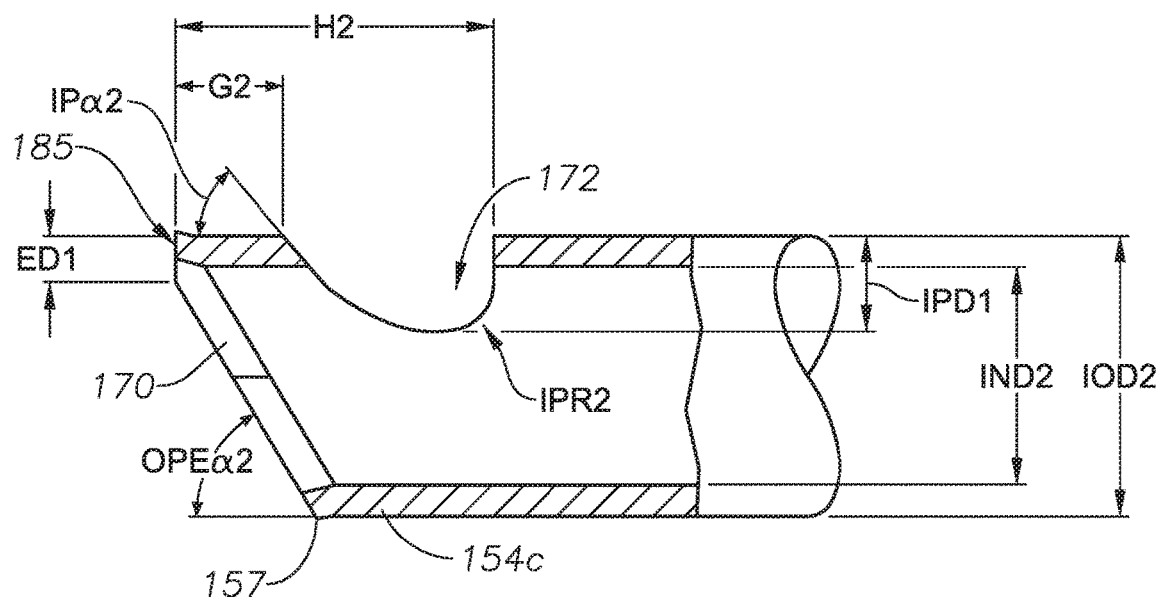

As seen in FIG. 15b, the inner tube proximal port to edge measurement H2 may be approximately 0.0138 inches. Other inner tube proximal port to edge measurements H2 are also contemplated (e.g., approximately in a range of 0.0083 to 0.019 inches or approximately in a range of 0.012 to 0.016 inches). The inner tube distal port to edge measurement G2 may be approximately 0.0047 inches. Other inner port to edge measurements G2 are also possible (e.g., G2 may be approximately in a range of 0.0028 inches to 0.0066 inches or approximately in a range of 0.004 to 0.0055 inches). The port edge angle IP$\alpha$2 may be approximately 50 degrees. Other port edge angles IP$\alpha$2 are also contemplated (e.g., approximately in a range of 30 to 70 degrees or approximately in a range of 40 to 60 degrees). The outer port edge angle OPE$\alpha$2 may be approximately 59 degrees. Other port edge angles OPE$\alpha$2 are also contemplated (e.g., approximately in a range of 35 to 85 degrees or approximately in a range of 50 to 70 degrees). The inner tube flattened edge feature 185 may have a depth ED1 of approximately 0.002 inches. Other depths ED1 are also contemplated (e.g., approximately in a range of 0.0012 to 0.0028 inches or approximately in a range of 0.0017 to 0.0023 inches). The inner port depth IPD1 may be approximately 0.004 inches. Other inner port depths IPD1 are also contemplated (e.g., approximately in a range of 0.0024 to 0.0056 inches or approximately in a range of 0.0034 to 0.0046 inches). The proximal edge of the inner port may have a radius IPR2 of approximately 0.00205 inches. Other proximal edge radius IPR2 are also contemplated (e.g., approximately in a range of 0.00123 to 0.0287 inches or approximately in a range of 0.00174 to 0.00236 inches). The inner tube inner diameter IND2 may be approximately 0.0096 inches. Other inner tube inner diameters IND2 are also contemplated (e.g., approximately in a range of 0.0058 to 0.013 inches or approximately in a range of 0.0082 to 0.011 inches). The inner tube outer diameter IOD2 of the outer cutting tube 152 may be approximately 0.0122 inches. Other outer diameters IOD2 are also contemplated (e.g., approximately in a range of 0.0073 to 0.017 inches or approximately in a range of 0.010 to 0.014 inches).

Figure 15C:
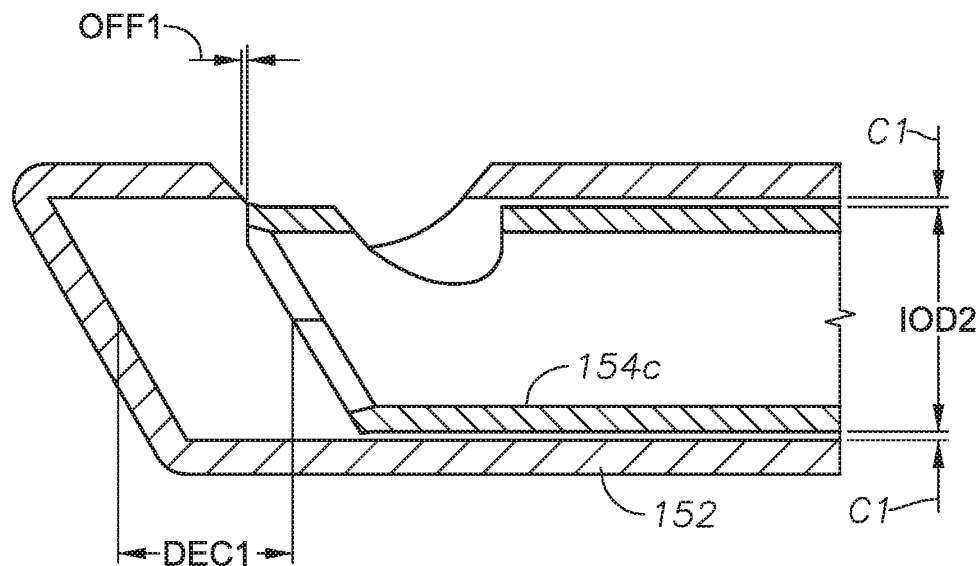
Figure 15D:
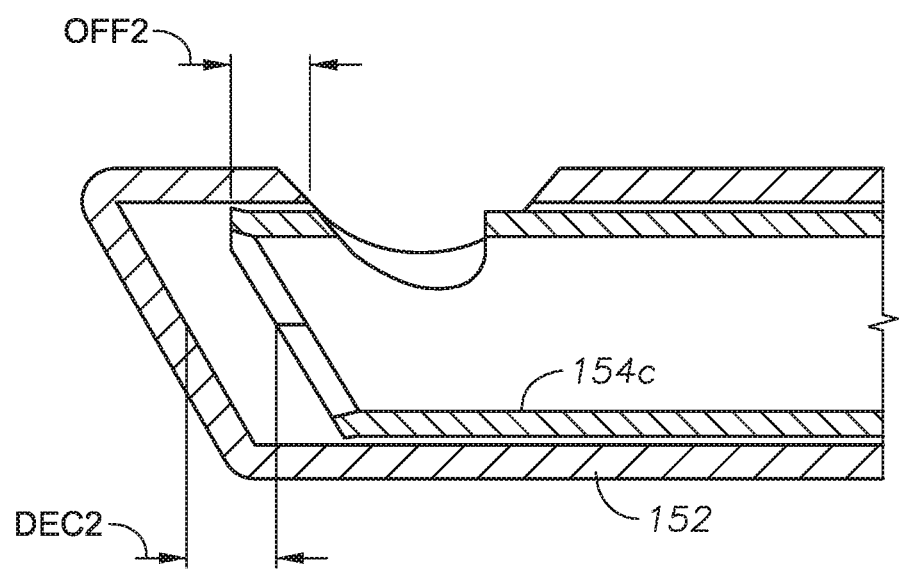

FIG. 15c illustrates the inner cutting tube 154c and outer cutting tube 152 in a cutting cycle at a point where an edge offset OFF1 is approximately 0 inches. FIG. 15d illustrates the inner cutting tube 154c and outer cutting tube 152 in a cutting cycle at a point where an edge offset OFF2 is approximately 0.0043 inches. With the edge offset OFF1 of approximately 0 inches, the distal edge clearance DEC1 between the distal edge of the inner tube 154c and the inside distal surface of the outer tube 152 may be approximately 0.0084 inches. Other distal edge clearance DEC1 are also contemplated (e.g., approximately in a range of 0.0050 to 0.012 inches or approximately in a range of 0.0071 to 0.0097 inches). With the edge offset OFF2 of approximately 0.0043 inches, the distal edge clearance DEC2 between the distal edge of the inner tube 154c and the inside distal surface of the outer tube 152 may be approximately 0.0041 inches. Other distal edge clearance DEC2 are also contemplated (e.g., approximately in a range of 0.0025 to 0.0057 inches or approximately in a range of 0.0035 to 0.0047 inches). As further seen in FIG. 15c, the tube clearance C1 between the inner tube 154c and the outer tube 152 may be approximately 0.0005 inches. Other tube clearances C1 are also contemplated (e.g., approximately in a range of 0.0003 to 0.0007 inches or approximately in a range of 0.00042 to 0.00058 inches).

Figure 16A:
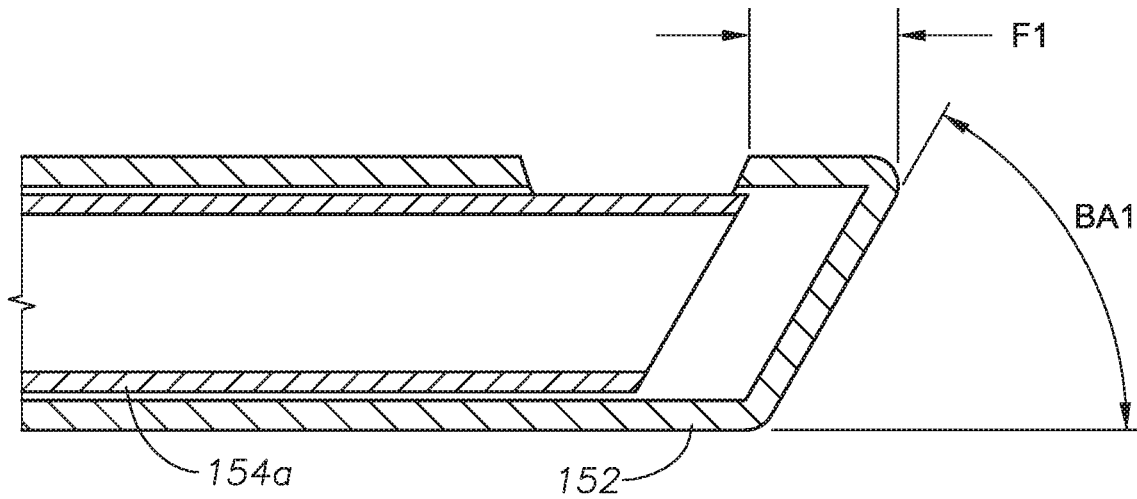
FIGS. 16a-d illustrate configurations of the outer cutting tube and inner cutting tube of the vitrectomy probe, according to various embodiments.
Figure 16B:
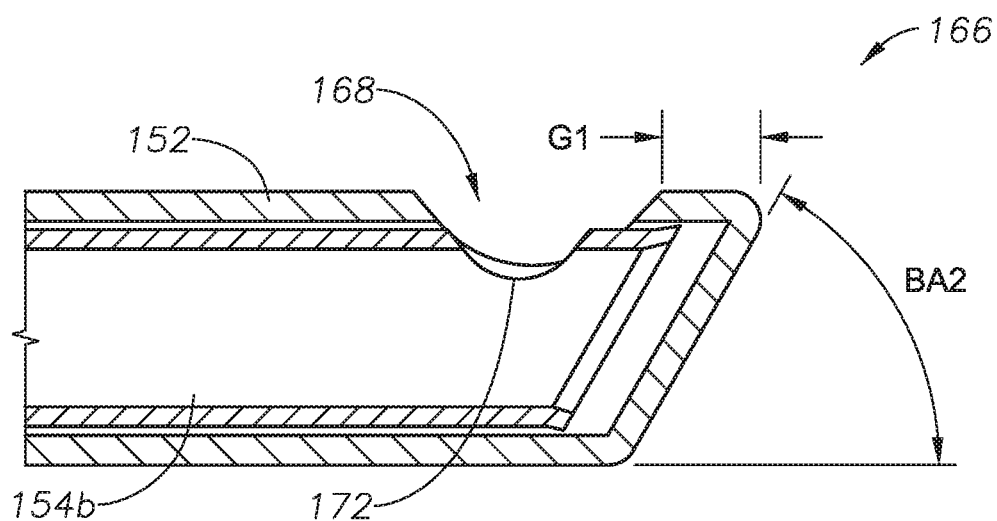
Figure 16C:
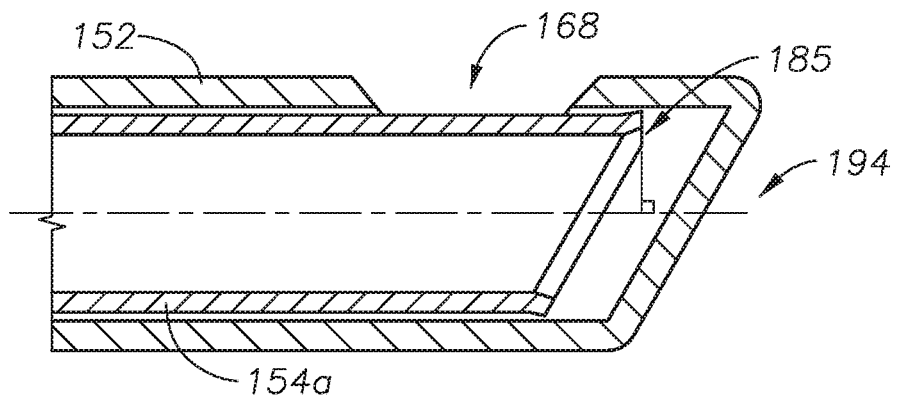
Figure 16D:
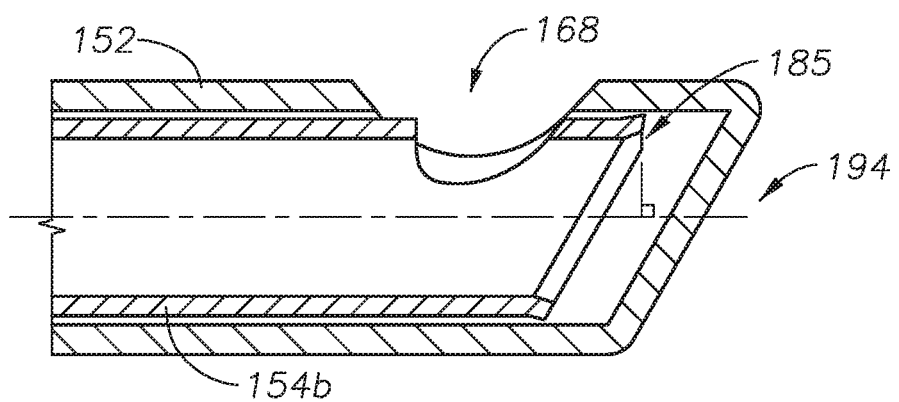

As seen in FIGS. 16a-d, in some embodiments, port to distal probe tip measurement F1 may be approximately in a range of 0.003 to 0.012 inches. As another example, F1 may be approximately in a range of 0.001 to 0.015 inches, approximately in a range of 0.003 to 0.015 inches, approximately in a range of 0.003 to 0.0085 inches, approximately in a range of 0.005 to 0.025 inches, or approximately in a range of 0.008 to 0.010 inches. In some embodiments, bevel angle BA1 and BA2 may be approximately in a range of 15 to 75 degrees. As another example, bevel angles BA1 and BA2 may be approximately in a range of 5 to 90 degrees. In some embodiments, G1 may be approximately 0.006 inches. Other G1 measurements are also contemplated (e.g., approximately in a range of 0.0035 to 0.0085 inches or approximately in a range of 0.005 to 0.007 inches). As seen in FIGS. 16c-d, embodiments of the inner cutting tube 154 may include a flat upper edge 185, perpendicular (or, for example, approximately in a range of 70-110 degrees) to an inner tube longitudinal axis 194, on the portion of the inner cutting tube 154 that cuts across the outer port side opening 168. Other angles for the flat upper edge are also contemplated. In some embodiments, the flat upper edge 185 may decrease the potential of the inner cutting tube 154 snagging or "hanging" up on the outer cutting tube 152 as the inner cutting tube 154 shears back and forth across the outer port side opening 168. As seen in FIGS. 16c-d, the distal portions of the inner cutting tube 154 may include the flared edge. In some embodiments, the inner cutting tube 154 may not be flared.

Figure 17:
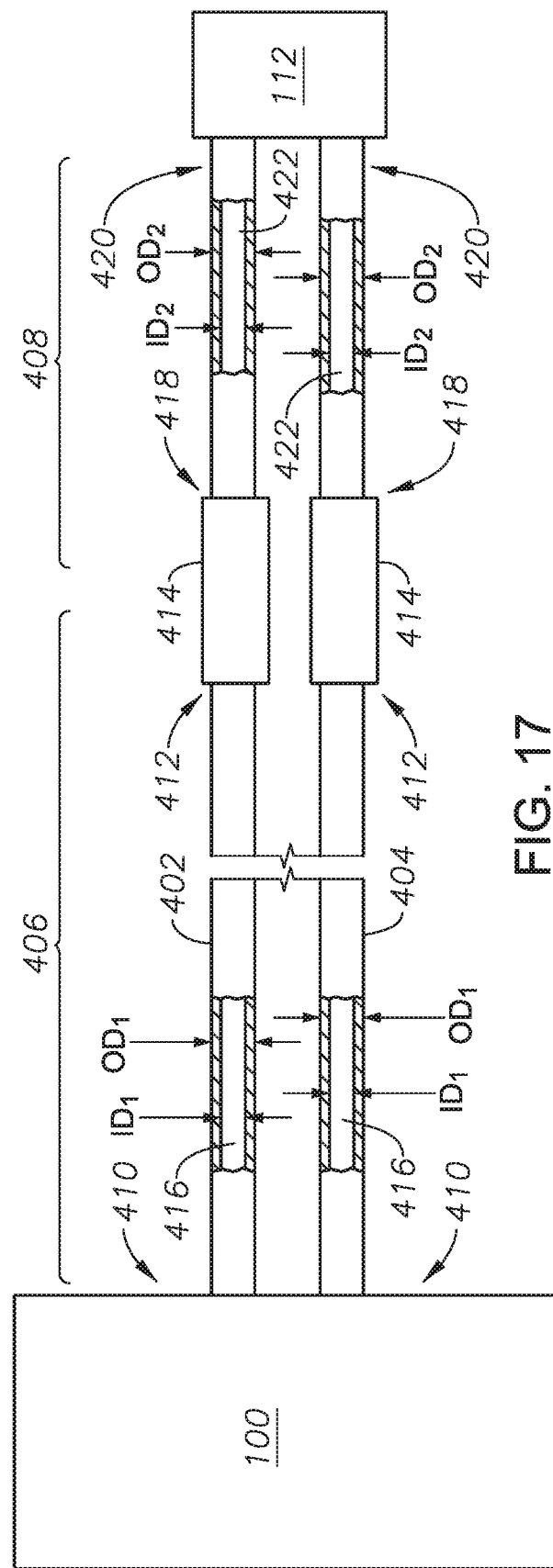
FIG. 17 is an illustration of a partial cross-sectional view of stepped pneumatic drive lines usable with the surgical system shown in FIG. 2, according to an embodiment.

FIG. 17 is an illustration of a partial cross-sectional view of stepped pneumatic drive lines usable with surgical console 100 to drive vitrectomy probe 112. As shown, surgical console 100 and vitrectomy probe 112 may be coupled to stepped pneumatic drive lines 402 and 404 (which may be used in place of pneumatic tubes 1002a-b). Stepped pneumatic drive lines 402 and 404 may be used in system 100 to drive the vitrectomy probe 112.

Stepped pneumatic drive line 402 will be described below. The features discussed with respect to stepped pneumatic drive line 402 may be present in and equally applicable to stepped pneumatic drive line 404. As such, similar reference numerals have been used in FIG. 17 to identify similar features with respect to stepped pneumatic drive lines 402 and 404.

Also, even though FIG. 17 shows two separate stepped pneumatic drive lines 402 and 404 powering vitrectomy probe 112, other embodiments utilize a single stepped pneumatic drive line or more than two stepped pneumatic drive lines. Thus, no limitation to the number of stepped pneumatic drive lines is implied herein to power vitrectomy probe 112.

Stepped pneumatic drive line 402 may have a first segment 406 and a second segment 408. The first segment 406 may have a proximal end 410 that is coupled to surgical console 100 via console ports and a distal end 412 that is coupled to the second segment 406 via a sleeve 414, or coupler. Additionally, the first segment may include an internal bore 416, or passageway extending from the proximal end 410 to the distal end 412 of the first segment 406.

Although sleeve 414 is shown coupling the first segment 406 and the second segment 408, it is contemplated that any other means can be used to couple the two segments together. For example, in other embodiments one of the segments may be configured to be slid into the other segment thereby coupling the segments without the use of sleeve 414. Additionally, in other embodiments, the pneumatic drive line 402 may be manufactured as a continuous drive line having the two or more segments with the stepped configuration. In such an embodiment, the pneumatic drive line may not require the sleeve coupling the segments because the segments have been manufactured into a continuous drive line having the stepped configuration.

As shown, first segment 406 may have a substantially constant outside diameter OD1 from the proximal end 410 to the distal end 412 of the first segment 406. By way of example, and not by limitation, OD1 may be about 0.250 inches. Moreover, OD1 may range from about 0.15 inches to about 0.5 inches. However, other dimensions for OD1 are contemplated thereby no implied limitation is set forth herein.

Additionally, internal bore 416 of first segment 406 may have a substantially constant inside diameter ID1 extending from the proximal end 410 to the distal end 412 of the first segment 406. By way of example, and not by limitation, ID1 may be about 0.150 inches. Moreover, ID1 may range from about 0.1 inches to about 0.3 inches. However, other dimensions for ID1 are contemplated thereby no implied limitation is set forth herein.

Second segment 408 may have a proximal end 418 that is coupled to the first segment 406 via sleeve 414 and a distal end 420 that is coupled to vitrectomy probe 112. Additionally, the second segment 408 may include an internal bore 422, or passageway extending from the proximal end 418 to the distal end 420 of the second segment 408.

As shown, second segment 408 may have a substantially constant outside diameter OD2 from the proximal end 418 to the distal end 420 of the second segment 408. By way of example, and not by limitation, OD2 may be about 0.125 inches. Furthermore, OD2 may range from about 0.05 inches to about 0.20 inches. However, other dimensions for OD2 are contemplated thereby no implied limitation is set forth herein.

Additionally, internal bore 422 of second segment 408 may have a substantially constant inside diameter ID2 extending from the proximal end 418 to the distal end 420 of the second segment 408. By way of example, and not by limitation, ID2 may be about 0.06 inches. Furthermore, ID2 may range from about 0.01 inches to about 0.150 inches. However, other dimensions for ID2 are contemplated thereby no implied limitation is set forth herein.

Accordingly, the second segment 408 may be "stepped" down relative to the first segment 406. In that regard, the outside diameter OD1 of the first segment 406 may be greater than the outside diameter OD2 of the second segment 408. Moreover, the inside diameter ID1 of the first segment 406 may be greater than the inside diameter ID2 of the second segment 408. Therefore, because the second segment 408 may be "stepped" down from the first segment 406, the passageway extending through stepped pneumatic drive line 402 may have a non-uniform cross-section and/or diameter as the pneumatic drive line extends from surgical console 100 to vitrectomy probe 112. While two segments are shown, in some embodiments, any number of segments may be used (e.g., 3, 4, 5, etc.) In some embodiments, the segments may have an increasing internal diameter closer to the console 100. In some embodiments, the outside diameter may also change (e.g., increase for the segments closer to the console) with each segment (or may remain the same).

Based on this stepped configuration, stepped pneumatic drive line 402 may increase the performance of vitrectomy probe 112 in comparison to other pneumatic instruments using traditional pneumatic drive line tubing. As discussed above, traditional pneumatic drive line tubing may have a constant inside diameter along the length of the tubing. Thus, the size of the passageway within the tubing may remain the same as the pressurized gas travels from the surgical console to the surgical instrument. By contrast, stepped pneumatic drive line 402 may have a non-constant or non-uniform inside diameter (or cross-section) along the length of the drive line. The use of a non-constant inside diameter may allow stepped pneumatic drive line 402 to be optimized based on its functional needs along its length. Because stepped pneumatic drive line 402 may be considered closed at its end coupled to vitrectomy probe 112 and is being driven from the end of the line coupled to console 100, the driven end of stepped pneumatic drive line 402 may have a higher gas flow requirement. Thus, in order to optimize gas flow, the driven end of stepped pneumatic drive line 402 may have a larger diameter than the closed end.

Here, first segment 406 may have a larger inside diameter ID1 for internal bore 416 than the inside diameter ID2 for internal bore 422 of segment 408. As such, internal bore 416 may allow for a larger volume of pressurized gas to be received into the line from console 100 where high flow of pressured gas is most important in order to optimize pneumatic performance.

Additionally, as discussed above, the use of a non-constant inside diameter may allow stepped pneumatic drive line 402 to be optimized based on its functional needs along its length. In that regard, because traditional pneumatic drive lines have constant diameters, the portion of the drive line adjacent the vitrectomy probe 112 may have the same large inside diameter required at the other end being driven by the surgical console 100. As such, the tubing may have a larger than ideal size and mass and as a result the tubing may typically not be as flexible as would be desirable near the vitrectomy probe 112.

Stepped pneumatic drive line 402 may address this issue. As discussed above, stepped pneumatic drive line 402 may include second segment 408 having a smaller inside diameter ID2 and outside diameter OD2 than the inside diameter ID1 and outside diameter OD1 of segment 406. As such, stepped pneumatic drive line 402 may provide a smaller drive line (e.g. second segment 408) adjacent the vitrectomy probe 112 where high flexibility and low mass may be important for a user of vitrectomy probe 112. In some embodiments, the stepped pneumatic drive line may include a larger diameter in the pneumatic line segment closer to the surgical console 100 while having a step down in diameter (e.g., via a connector) with the last approximately 12 inches (proximal to the vitrectomy probe 112) being approximately 0.125 inches in outer diameter and 0.06 inches in inner diameter (other lengths of last segments (e.g., greater or less than 12 inches) and other diameters are also contemplated). Therefore, stepped pneumatic drive line 402 tubing may be configured to optimize pneumatic performance with larger diameters near the console 100 while providing greater flexibility and low mass near the vitrectomy probe 112.

Figure 18:
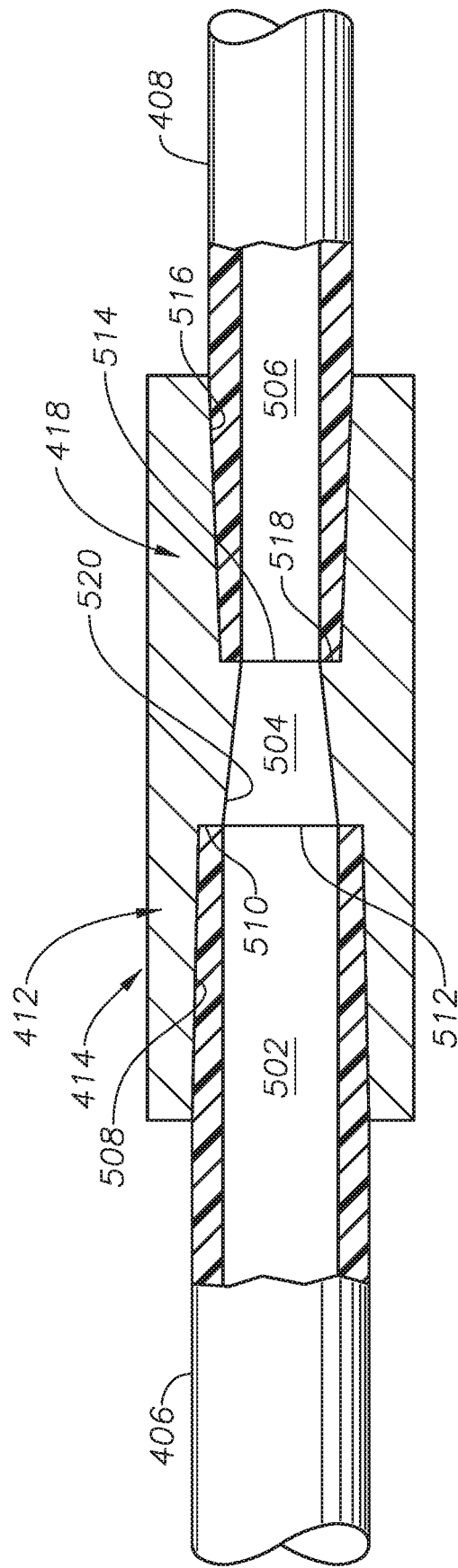
FIG. 18 is an illustration of a partial cross-sectional view of a sleeve coupling the stepped pneumatic drive line shown in FIG. 17, according to an embodiment.

FIG. 18 shows a partial cross-sectional view of sleeve 414 coupling the distal end 412 of the first segment 406 to the proximal end 418 of the second segment 408. As shown, sleeve 414 may have a proximal bore 502, connecting bore 504, or middle bore, and a distal bore 506. Proximal bore 502 may be sized and shaped for receiving distal end 412 of the first segment 406.

Moreover, proximal bore 502 is defined in part by interior surface 508 of sleeve 414. In that regard, interior surface 508 may be tapered or sloped towards connecting bore 504. As a result, distal end 412 of the first segment 406 may be coupled to sleeve 414 via a press-fit or sealing engagement by the tapered interior surface 508 applying a coupling force against the distal end 412.

Additionally, proximal bore 502 may include stops 510. Stops 510 may prevent the distal end 412 from extending into connecting bore 504. In that regard, distal end 412 of the first segment 406 may abut against the stops 510 when fully inserted into sleeve 414. Thus, stops 510 may prevent over insertion of distal end 412 into sleeve 414.

Distal bore 506 may be sized and shaped for receiving proximal end 418 of the second segment 408. Distal bore 506 may be defined in part by interior surface 516 of sleeve 414. In that regard, interior surface 516 may be tapered or sloped towards connection bore 504. As a result, proximal end 418 of the second segment 408 may be coupled to sleeve via a press-fit or sealing engagement by the tapered interior surface applying a coupling force against the proximal end 418.

Additionally, distal bore 506 may include stops 518. Stops 518 may prevent the proximal end 418 from extending into connecting bore 504. In that regard, proximal end 418 of the second segment 408 may abut against the stops 518 when fully inserted into sleeve 414. Thus, stops 518 may prevent over insertion of proximal end 418 into sleeve 414.

As shown, connecting bore 504 may be positioned between the proximal bore 502 and the distal bore 506. Connecting bore may have a conical shape. In that regard, interior surface 520 may define connecting bore 504 and may taper toward distal bore 506. As such, opening 512 of connecting bore 504 adjacent the proximal bore 502 may have a larger diameter than opening 514 adjacent the distal bore 506. Moreover, opening 512 may have a diameter substantially similar to the inside diameter ID1 of internal bore 416 of the first segment 406. Additionally, opening 514 may have a diameter substantially similar to the inside diameter ID2 of internal bore 422 of the second segment 408. Because of the sizing of openings 512 and 514 and the conical shape of connecting bore 504, a seal may be formed between internal bore 416 of the first segment and internal bore 422 of the second segment 408 that enables pressurized gas to flow therethrough.

Other tapered tubing is also contemplated. For example, tapered pneumatic drive line may continuously taper from the surgical console 100 to the vitrectomy probe 112. In other words, an exterior surface of the pneumatic drive line and an interior surface defining a bore may both continuously taper from a proximal end to a distal end of a tapered pneumatic drive line. In some embodiments, the interior surface may taper while the exterior surface remains constant.

Figure 19:
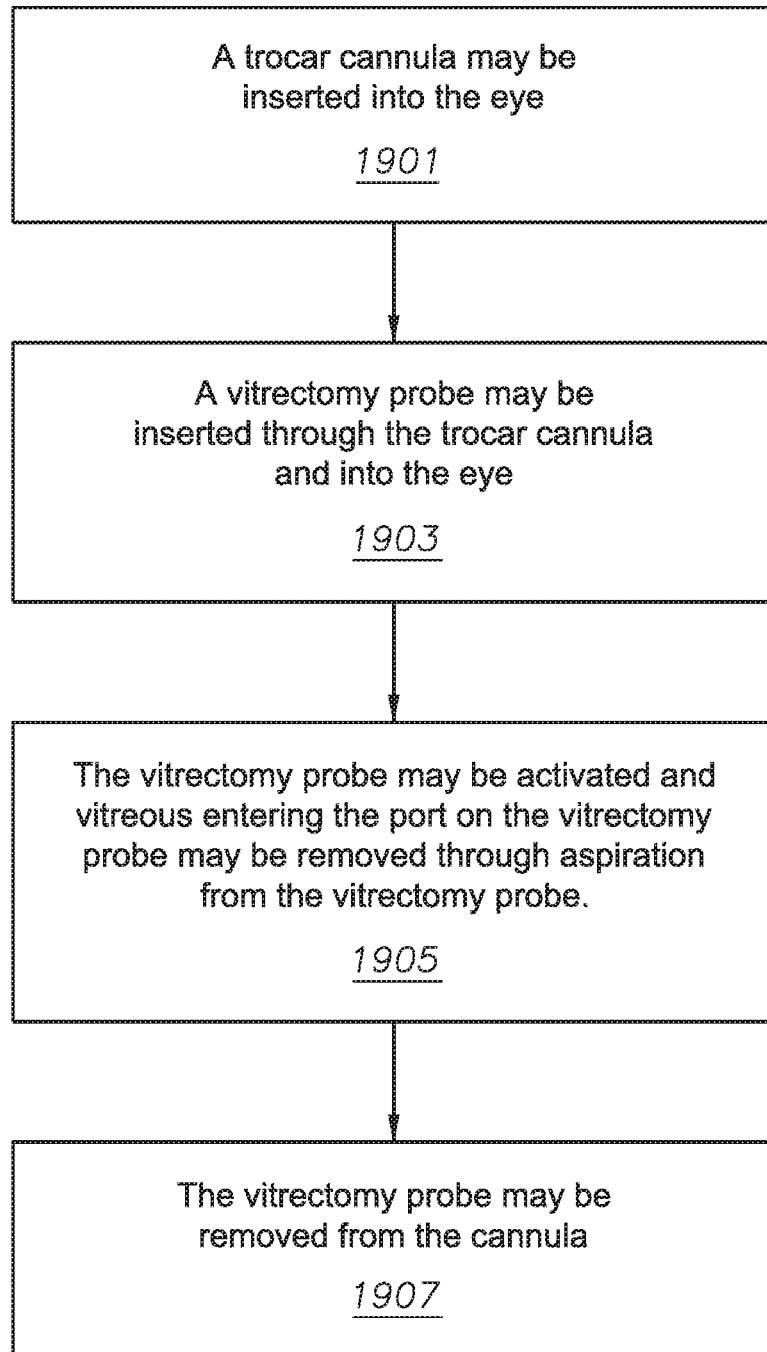
FIG. 19 illustrates a flowchart of a method for operating a vitrectomy probe, according to an embodiment.

FIG. 19 illustrates a flowchart of a method for operating the vitrectomy probe, according to an embodiment. The elements provided in the flowchart are illustrative only. Various provided elements may be omitted, additional elements may be added, and/or various elements may be performed in a different order than provided below.

At 1901, a trocar cannula may be inserted into the eye. In some embodiments, the trocar cannula may be inserted into a region of the eye that will allow instruments inserted through the trocar cannula to access the vitreous and retina.

At 1903, a vitrectomy probe may be inserted through the trocar cannula and into the eye.

At 1905, the vitrectomy probe may be activated and vitreous entering the port on the vitrectomy probe may be removed through aspiration from the vitrectomy probe.

At 1907, the vitrectomy probe may be removed from the cannula.

Various modifications may be made to the presented embodiments by a person of ordinary skill in the art. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A vitrectomy probe, comprising:
   an outer cutting tube with an outer port side opening;
   an inner cutting tube, positioned inside the outer cutting tube, wherein the inner cutting tube has an open distal end having a cutting edge;
   wherein the inner cutting tube further comprises a distal side port with a distal side port cutting edge positioned on the distal side port such that as the inner cutting tube retracts inside the outer cutting tube, tissue entering the outer port side opening also enters the distal side port of the inner cutting tube to be cut by the distal side port cutting edge as the inner cutting tube is retracted in the outer cutting tube;
   a diaphragm coupled to the inner cutting tube, wherein the diaphragm is located inside a drive chamber and the diaphragm is configured to move back and forth inside the drive chamber as air is alternately supplied and vented on either side of the diaphragm in the drive chamber;
   wherein movement of the diaphragm causes the inner cutting tube to oscillate inside the outer cutting tube such that the open distal end of the inner cutting tube moves back and forth across the outer port side opening to cut tissue entering the outer port side opening;
   wherein the diaphragm comprises an open-stroke side with a first contact surface that contacts an inner drive chamber wall when the inner cutting tube is in a retracted position;
   wherein the diaphragm comprises an closed-stroke side with a second contact surface that contacts an opposing inner drive chamber wall when the inner cutting tube is in an extended position; and
   wherein the first contact surface comprises a material with a lower hardness than the second contact surface.

2. The vitrectomy probe of claim 1, wherein the first contact surface comprises silicone and the second contact surface comprises polycarbonate or polysulfone.

3. The vitrectomy probe of claim 1, wherein the outer cutting tube has a beveled closed end with a degree of bevel approximately in a range of 20 to 80 degrees as measured from the beveled closed end to an extended back surface line of the outer cutting tube that is opposite the outer port side opening.

4. The vitrectomy probe of claim 3, wherein a port edge tip to retinal (PTRD) distance is approximately in a range of 0.004 to 0.009 inches and a port edge to distal probe tip measurement (PTTD) is approximately in a range of 0.005 to 0.010 inches with approximately a 60 degree bevel as measured from the beveled closed end to an extended back surface line of the outer cutting tube that is opposite the outer port side opening.

5. The vitrectomy probe of claim 1, further comprising an aspiration tubing coupled to the inner cutting tube to apply a vacuum to the inner cutting tube and wherein the aspiration tubing comprises a first aspiration tubing with a first aspiration tubing hardness, configured to be coupled to a surgical console, and a second aspiration tubing coupled to the first aspiration tubing and the vitrectomy probe, wherein the second aspiration tubing has a second aspiration tubing hardness that is less than the first aspiration tubing hardness.

6. The vitrectomy probe of claim 5, wherein the first aspiration tubing has an inner diameter of approximately 0.060 inches and the first aspiration tubing hardness of approximately 80 Shore A and the second aspiration tubing has an inner diameter of approximately 0.060 inches and the second aspiration tubing hardness of approximately 40 Shore A;
   wherein the first aspiration tubing is approximately 79 inches long and wherein the second aspiration tubing is approximately 5 inches long and is coupled to the vitrectomy probe on a distal end and coupled to the first aspiration tubing on a proximal end.

7. The vitrectomy probe of claim 1, wherein the outer port side opening has a proximal port edge angle approximately in a range of 40 to 60 degrees and a distal port edge angle approximately in a range of 35 to 55 degrees.

8. The vitrectomy probe of claim 1, further comprising a pneumatic drive line coupling the vitrectomy probe to a surgical console, the pneumatic drive line having an internal bore configured to deliver the air to the vitrectomy probe, the internal bore having a non-uniform cross-section along a length of the pneumatic drive line, wherein the pneumatic drive line comprises a first segment and a second segment, the first segment defining a first passageway having a first diameter and the second segment defining a second passageway having a second diameter, the first diameter being different than the second diameter.

9. A vitrectomy probe, comprising:
   an outer cutting tube with an outer port side opening and a beveled closed end;

an inner cutting tube, positioned inside the outer cutting tube, wherein the inner cutting tube has an open distal end having a cutting edge and a distal side port with a distal side port cutting edge positioned on the distal side port such that as the inner cutting tube retracts inside the outer cutting tube, tissue entering the outer port side opening also enters the distal side port of the inner cutting tube to be cut by the distal side port cutting edge as the inner cutting tube is retracted in the outer cutting tube;

a diaphragm coupled to the inner cutting tube, wherein the diaphragm is located inside a drive chamber and the diaphragm is configured to move back and forth inside the drive chamber as air is alternately supplied and vented on either side of the diaphragm in the drive chamber;

wherein movement of the diaphragm causes the inner cutting tube to oscillate inside the outer cutting tube such that the open distal end of the inner cutting tube moves back and forth across the outer port side opening to cut tissue entering the outer port side opening; and wherein the inner cutting tube comprises a flat upper edge, approximately perpendicular to an inner tube longitudinal axis, on the portion of the inner cutting tube that cuts across the outer port side opening;

wherein movement of the diaphragm causes the inner cutting tube to oscillate inside the outer cutting tube such that the open distal end of the inner cutting tube moves back and forth across the outer port side opening to cut tissue entering the outer port side opening;

wherein the diaphragm comprises an open-stroke side with a first contact surface that contacts an inner drive chamber wall when the inner cutting tube is in a retracted position;

wherein the diaphragm comprises an closed-stroke side with a second contact surface that contacts an opposing inner drive chamber wall when the inner cutting tube is in an extended position; and wherein the first contact surface comprises a material with a lower hardness than the second contact surface.

10. The vitrectomy probe of claim 9, wherein the outer port side opening has a proximal port edge angle approximately in a range of 40 to 60 degrees and a distal port edge angle approximately in a range of 35 to 55 degrees.

11. The vitrectomy probe of claim 9, further comprising an aspiration tubing coupled to the inner cutting tube to apply a vacuum to the inner cutting tube; and wherein the aspiration tubing comprises a first aspiration tubing with a first aspiration tubing hardness, configured to be coupled to a surgical console, and a second aspiration tubing coupled to the first aspiration tubing and the vitrectomy probe, wherein the second aspiration tubing has a second aspiration tubing hardness that is less than the first aspiration tubing hardness.

12. The vitrectomy probe of claim 11, wherein the first aspiration tubing has an inner diameter of approximately 0.060 inches and the first aspiration tubing hardness of approximately 80 Shore A and the second aspiration tubing has an inner diameter of approximately 0.060 inches and the second aspiration tubing hardness of approximately 40 Shore A; and wherein the first aspiration tubing is approximately 79 inches long and wherein the second aspiration tubing is approximately 5 inches long and is coupled to the vitrectomy probe on a distal end and coupled to the first aspiration tubing on a proximal end.

13. The vitrectomy probe of claim 9, further comprising a pneumatic drive line coupling the vitrectomy probe to a surgical console, the pneumatic drive line having an internal bore configured to deliver the air to the vitrectomy probe, the internal bore having a non-uniform cross-section along a length of the pneumatic drive line, wherein the pneumatic drive line comprises a first segment and a second segment, the first segment defining a first passageway having a first diameter and the second segment defining a second passageway having a second diameter, the first diameter being different than the second diameter.

14. The vitrectomy probe of claim 9, wherein a port edge tip to retinal (PTRD) distance for the outer port side opening is approximately in a range of 0.004 to 0.009 inches and a port edge to distal probe tip measurement (PTTD) for the outer port side opening is approximately in a range of 0.005 to 0.010 inches with approximately a 60 degree bevel as measured from the beveled closed end to an extended back surface line of the outer cutting tube that is opposite the outer port side opening.

* * * * *